United States Patent [19]

Wong

[11] Patent Number: 5,503,001

[45] Date of Patent: Apr. 2, 1996

[54] DETERMINATION OF PERMEABILITY OF POROUS MEDIA AND THICKNESS OF LAYERED POROUS MEDIA

[75] Inventor: Po-zen Wong, Amherst, Mass.

[73] Assignee: Gas Research Institute, Chicago, Ill.

[21] Appl. No.: 371,508

[22] Filed: Jan. 11, 1995

Related U.S. Application Data

[63] Continuation-in-part of Ser. No. 68,967, May 28, 1993, Pat. No. 5,417,104.

[51] Int. Cl.[6] ............................ F21B 49/00; G01V 3/18; G01N 15/08
[52] U.S. Cl. .......................... 73/38; 73/155; 324/351; 324/376; 324/353
[58] Field of Search ........................ 73/38, 155, 152; 324/353, 351, 376, 386, 366

[56] References Cited

U.S. PATENT DOCUMENTS

| | | | |
|---|---|---|---|
| 2,214,786 | 9/1940 | Bishop | 324/351 |
| 2,433,746 | 12/1947 | Doll | 324/353 |
| 2,550,005 | 4/1951 | Doll | 324/353 |
| 2,569,625 | 10/1951 | Wyllie | 324/351 |
| 2,592,125 | 4/1952 | Doll | 324/351 |
| 2,713,146 | 7/1955 | Doll | 324/351 |
| 2,814,017 | 11/1957 | Doll | 324/353 |
| 2,974,273 | 3/1961 | Vogel et al. | 324/353 |
| 3,243,695 | 3/1966 | Roark et al. | 324/376 |
| 3,302,101 | 1/1967 | Glanville | 324/376 |
| 3,599,084 | 8/1971 | Bakamjian | 324/353 |
| 3,599,085 | 8/1971 | Semmelink | 324/386 |
| 3,638,106 | 1/1972 | Cram | 324/351 |
| 3,691,456 | 9/1972 | Warren et al. | 324/351 |
| 4,427,944 | 1/1984 | Chandler | 324/523 |
| 4,573,342 | 3/1986 | Jones | 73/38 |
| 4,626,773 | 12/1986 | Kroeger et al. | 324/642 |
| 4,671,100 | 6/1987 | Doussiet | 73/38 |
| 4,686,477 | 8/1987 | Givens et al. | 324/366 |
| 4,730,162 | 3/1988 | Vinegar et al. | 324/362 |
| 4,769,606 | 9/1988 | Vinegar et al. | 324/366 |
| 4,791,822 | 12/1988 | Penny | 73/38 |
| 4,864,845 | 9/1989 | Chandler et al. | 73/38 |
| 4,868,751 | 9/1989 | Dogru et al. | 364/422 |
| 4,876,512 | 10/1989 | Kroeger et al. | 324/376 |
| 4,922,758 | 5/1990 | Penny | 73/38 |
| 4,961,343 | 10/1990 | Boone | 73/152 |
| 4,979,393 | 12/1990 | Leung et al. | 73/155 |
| 5,010,301 | 4/1991 | Leung et al. | 324/376 |
| 5,237,854 | 8/1993 | Jones | 73/38 |
| 5,269,180 | 12/1993 | Dave et al. | 73/38 |
| 5,417,104 | 5/1995 | Wong | 73/38 |

FOREIGN PATENT DOCUMENTS 0043768 1/1982 European Pat. Off. .

OTHER PUBLICATIONS

The Leading Edge, Dec. 1993, pp. 1169–1173, A. H. Thompson et al. "Geophysical applications of electrokinetic conversion".

*Primary Examiner*—Hezron E. Williams
*Assistant Examiner*—J. David Wiggins
*Attorney, Agent, or Firm*—Speckman, Pauley & Fejer

[57] ABSTRACT

Process and apparatus for determination of permeability of porous media and thickness of layered porous media by measurement at finite frequency of streaming potential and electro-osmotic induced voltage due to applied finite frequency pressure oscillations and alternating current, respectively. The distance between application and measurement of the alternating signals at a finite frequency is small compared to the wave length. A plurality of spaced measurement electrodes provides measurement of the penetration depth of applied pressure oscillations for determination of thickness of porous layers and to largely remove the effect due to mudcake on a borehole in streaming potential measurements.

45 Claims, 13 Drawing Sheets

DETERMINATION OF PERMEABILITY OF POROUS MEDIA AND THICKNESS OF LAYERED POROUS MEDIA

This application is a continuation in part application of application Ser. No. 08/068,967 filed on May 28, 1993, which has now become U.S. Pat. No. 5,417,104 as of May 23, 1995.

BACKGROUND OF THE INVENTION

1. Field of the Invention

This invention relates to a process and apparatus for determination of permeability of porous media and thickness of layered porous media, such as underground formations, especially shaly formations having low permeability. Permeability may he determined according to this invention by measurement at a finite frequency of streaming potential and electro-osmotic induced pressure due to applied finite frequency pressure oscillations and alternating current, respectively, with use of both measurement coefficients in conjunction with electrical conductivity, which may be measured simultaneously or separately, to obtain the formation permeability. Permeability may also he obtained directly from measurement of the relaxation frequency of electro-osmosis coefficient alone. Thickness of layered porous materials, such as mudcake lining bore holes and layered porous rock, may be determined by measurement of streaming potential coefficient alone over a range of frequencies. In the apparatus of this invention, the differential pressure and voltage may be measured at substantially the point where pressure oscillations and sitemaring current are applied, that is, the distance between application and measurement electrodes is small compared to the sonic or subsonic wave length and the electrodes are removed from formation fluid flow paths. The apparatus may have a plurality of spaced measurement electrodes to provide measurement of the penetration depth of applied pressure oscillations for determination of thickness of layers of porous media and to largely remove the effect due to the mudcake in streaming potential measurements.

2. Description of Related Art

Several prior patents teach application of pulsed pressure and measurement of an a.c. signal of defined frequency in the measurement of streaming potential in a porous underground formation: U.S. Pat. No. 2,433,746 teaches vigorous vibration of a down hole apparatus to generate pressure oscillations for measurement, with one electrode down the borehole and the other at the surface, of the potential to ascertain the streaming potential; U.S. Pat. No. 2,550,005 teaches a modification of the method taught by the U.S. Pat. No. 2,433,746 patent by pressurizing the entire well to produce the periodic pulses in the borehole liquid; and U.S. Pat. No. 3,599,085 teaches use of a sonic transducer periodically exciting a formation at low frequencies to cause periodic electrokinetic potentials which are measured at a location near the transducer and at a location spaced from the transducer, the ratio of the measured potentials being related to the electrokinetic skin depth to provide an indication of permeability of the formation. U.S. Pat. No. 4,427,944 teaches application of pressure of alternating polarity to the formation and measurement of the generated transient streaming potentials in the time domain to estimate the characteristic response time which is inversely proportional to the formation permeability.

U.S. Pat. No. 4,864,845 teaches in-situ rock permeability measurements using an electronic field permeameter with a microcomputer which automatically turns on a gas supply, senses when a steady-state is reached, collects and records pressure and flow rate, and shuts off the gas supply immediately upon completion of the measurement. The injection pressure and flow rate of the gas is used to determine permeability.

U.S. Pat. No. 2,814,017 teaches measurement of the difference in phase between periodic pressure waves passed through a formation and potentials generated by the oscillatory motion of the formation caused by these pressure waves and, conversely, application of a periodically varying electric current to the formation fluid to generate periodic pressure waves in the formation by electro-osmosis. Measurements of the phase shift in the frequency domain between the generating and generated quantities is said to be a measure of permeability of the formation. U.S. Pat. No. 4,730,162 teaches time domain induced polarization with a square wave of alternating polarity being applied intermittently and alternately for induced polarization logging.

U.S. Pat. No. 3,302,101 teaches measurement of electroresistivity of a core sample maintained under constant pressure with power supplied by an alternating current and U.S. Pat. No. 4,686,477 teaches application of multi-frequency electric current to a sub-surface formation for ascertainment of the relation of resistivity versus frequency for characterization of rock lithology.

The methods taught by the prior art patents have many disadvantages. Neither the streaming potential nor the electro-osmotic measurement alone is a reliable indication of formation permeability, especially in formations of low permeability. Attempts to measure the streaming potential signal with electrodes at distances greater than one wavelength from each other are flawed since pressure oscillation propagates as a sound wave and the pressure difference would depend on both the magnitude and the phase of the wave and the streaming potential signal would be very low since considerable energy is lost to viscous dissipation over such a distance. Movement of the electrode in well fluid is disadvantageous since its own surface potential would be disturbed and oscillate at the same frequency causing an oscillating voltage much stronger than the streaming potential signal. Application of a d.c. flow to a formation and measurement of the response voltage in the time domain will not work in low permeability formations since the longer response time and very low streaming potential signal is dominated over by drifts of the electrodes' interfacial voltage over time. Measurement of a pressure signal resulting from the electro-osmotic effect would be even more difficult since it would be very weak and inseparable from the much larger voltage signal at the same frequency resulting from formation resistivity. Proposed measurement of the phase-shift in the frequency domain would be even more difficult than the suggested measurement of the response time in the time domain.

SUMMARY OF THE INVENTION

It is an object of this invention to overcome many of the disadvantages of prior streaming potential and electro-osmotic pressure measurements.

It is another object of this invention to provide a method of determining electro-osmosis coefficients at higher frequencies than previously described to shorten the time required for measurement.

It is yet another object of this invention to provide a method for determination of permeability of porous media directly from relaxation frequency of the electro-osmosis coefficient.

It is still another object of this invention to provide a method for determining thickness of layered porous materials, in particular, mudcake on the borehole wall and thin geological beds.

Another object of this invention is to provide an apparatus suitable for ascertainment by a single instrument of streaming potential and electro-osmosis coefficients and the penetration depth of the measurement.

In estimating reserves and in predicting producibility from both gas and oil underground deposits, it is important to know the permeability and physical parameters of rock formations. Streaming potential and electro-osmosis are known electrokinetic phenomena which result from the presence of surface charge in porous media and represent the coupling between fluid flow and electric current flow in such media. According to the invention as described in the parent application, Ser. No. 08/068,967, filed May 28, 1993, incorporated herein in its entirety by reference, a.c. measurement at the finite frequency of streaming potential and electro-osmotic induced voltage and pressure, respectively, results in coefficients $K_1$ and $K_2$, respectively, from which the zeta-potential ($\zeta$) which affects the surface conductivity and the throat size (R) which affects hydraulic permeability can be calculated. These parameters, $\zeta$ and R, may be used in interpretation methods to obtain the formation factor (F) and the permeability (k).

The apparatus of this invention overcomes disadvantages of prior dominating background d.c. voltage and noise in typical borehole environments which has prevented use of streaming potential and electro-osmotic measurements for evaluation of all types of formations, particularly those exhibiting low permeability. The undesired d.c. voltage arises from electrode-polarization inherent in instrument designs and spontaneous potential which is present in underground formations. The undesired noise arises from vibration of the logging tools and induced voltages from other parts of the electrical circuitry. Such sources of interfering voltages are generally larger than typical streaming potential and electro-osmosis signals, which are generally in the order of μV/PSI and mPSI/V, respectively, rendering such measurements impractical. The apparatus, generally, uses an electromechanical transducer to generate differential pressure oscillations between two points at a finite frequency and detects the pressure differential and streaming potential signal between the same two points near the source of the pressure application and at the same frequency using a lock-in amplifier or a digital frequency response analyzer. In a similar manner, for electro-osmosis measurement, a pair of electrodes applies an alternating current and the induced electro-osmosis pressure and applied voltage signals are detected at the same frequency and between the same two points near the source of a.c. current application. Because the apparatus of this invention measures the differential pressure in the porous media between two points at finite frequencies close to the source of applied pressure and current, it greatly reduces the effect of background caused by the hydrostatic pressure due to the depth of the formation being measured.

Higher frequencies may be used and permeability obtained directly by measuring the angular relaxation frequency of the electro-osmosis coefficient.

Thickness of layered porous materials, including mudcake lining bore holes, can be determined by measurement of streaming potential over a range of frequencies. The error in streaming potential measurements introduced by the mudcake can be largely removed by use of the plurality of measurement chambers in the pad-tool of one preferred embodiment of this invention.

BRIEF DESCRIPTION OF THE DRAWINGS

The above objects and advantages of this invention will become further apparent upon reading the detailed description of the preferred embodiments with reference to the drawings wherein.

DESCRIPTION OF PREFERRED EMBODIMENTS

Figure 1:
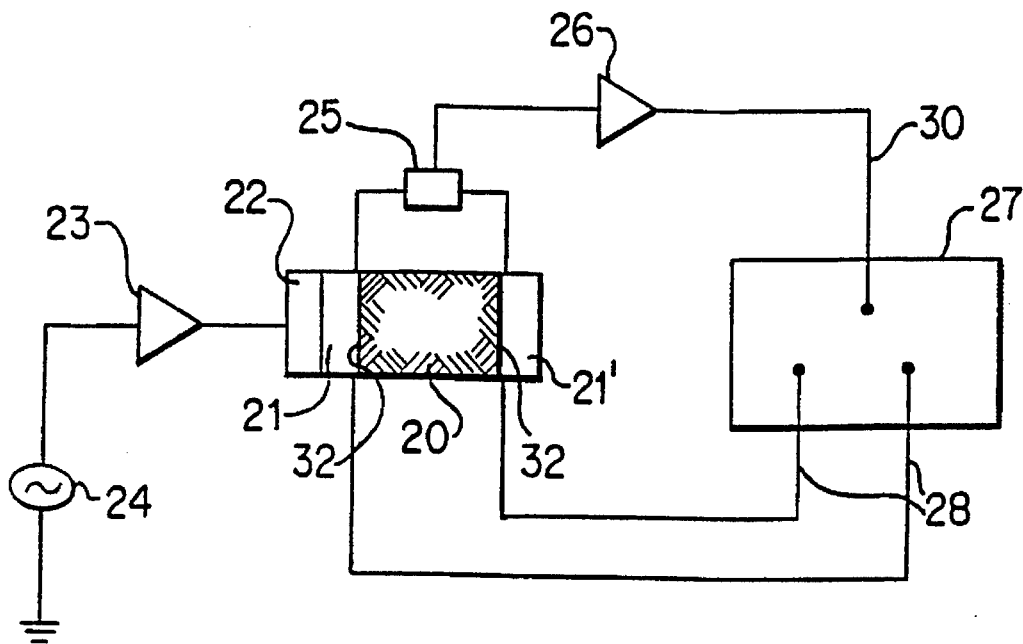
FIG. 1 is a simplified schematic showing an apparatus for measurement of induced streaming potential coefficient $K_1$ according to one embodiment of this invention.

Streaming Potential Coefficient $K_1$ may be obtained by a.c. measurement of streaming potential voltage induced by applied pressure oscillations at a finite frequency, as will be described in greater detail, by the relation:

$$K_1 = V_s/P_a \qquad \text{Eq. 1}$$

wherein $V_s$ is the measured induced streaming potential voltage and $P_a$ is the applied pressure.

Electro-osmosis Coefficient $K_2$ may be obtained by a.c. measurement of electro-osmotic pressure and applied voltage, as will be described in greater detail, by the relation:

$$K_2 = P_e/V_a \qquad \text{Eq. 2}$$

wherein $P_e$ is the measured electro-osmotic pressure and $V_a$ is the applied voltage.

At zero frequency, or d.c., these coefficients are related to formation properties in the following manner (in gaussian units):

$$K_1^o = \epsilon \zeta/4\pi\eta\sigma_w \qquad \text{Eq. 3}$$

$$K_2^o = 2\epsilon\zeta/\pi R^2 \qquad \text{Eq. 4}$$

where $\epsilon$ is the dielectric constant of the formation fluid, $\sigma_W$ is the conductivity of the fluid, and $\eta$ is the fluid viscosity, all of which can be easily determined for each formation by known laboratory analyses. The formation properties of interest, the pore size R and the pore surface potential $\zeta$, may be obtained from the measured $K_1^o$ and $K_2^o$ coefficients by the following relationships:

$$\zeta = (4\pi\eta\sigma_W/\epsilon)K_1^o \qquad \text{Eq. 5}$$

$$R = \sqrt{8\eta\sigma_w K_1^o/K_2^o} \qquad \text{Eq. 6}$$

These values are then used to obtain the formation factor F by the relation:

$$F = (\sigma_w + \alpha\zeta/R)/\sigma_r \qquad \text{Eq. 7}$$

where $\sigma_r$ is rock conductivity and e is a numerical constant that relates the surface potential $\zeta$ to the surface conductivity. The formation permeability k may be obtained by the relation:

$$k = \eta\sigma_r K_1^o/K_2^o \qquad \text{Eq. 8}$$

By obtaining streaming potential and electro-osmosis coefficients, ascertainment of rock conductivity ($\sigma_r$) by known methods, and fluid viscosity ($\eta$) which is known in practical situations, all quantities on the right hand side of Eq. 8 are determined and the equation can be solved for formation permeability. Streaming potential and electro-osmosis measurements can be made over a wide frequency range.

The higher order effect of streaming potential and electro-osmosis gives a measurable quadrature conductivity $\sigma''$ in low permeability formations, such as shaly sandstones. Using the apparatus as described in the patent application, Ser. No. 08/068,967 and shown in FIGS. 1–4, upon application of an a.c. current to the formation with a pair of electrodes and detection of the voltage drop across it with another pair of electrodes, a phase-sensitive lock-in amplifier or frequency response analyzer can separate the usual in-phase conductivity $\sigma'$ from the quadrature conductivity $\sigma''$. The quadrature conductivity $\sigma''$ is proportional to the surface conductivity, and hence proportional to the surface potential $\zeta$ according to the relationship:

$$\zeta = \sigma''/\beta \qquad \text{Eq. 9}$$

wherein $\beta$ is a numerical constant. The apparatus may be used to obtain pore surface potential $\zeta$ by streaming potential coefficient $K_1^o$, according to Eq. 5, or by a direct conductivity measurement as shown by Eq. 9. R may be determined by using Eq. 6. Streaming potential coefficient $K_1^o$ and electro-osmosis coefficient $K_2^o$ may be used alone to obtain $\zeta$, R, and $\sigma_W$ according to Equations 5, 6, and 9, or may be combined with conductivity to obtain formation permeability k according to Equation 8. Also, knowing $K_1^o$ and one of $\zeta$ or $\sigma_W$, the other can be determined according to Eq. 3. Often $\zeta$ is determined from core samples and a streaming potential measurement can be used to determine $\sigma_W$ in the formation by Eq. 3.

Figure 2:
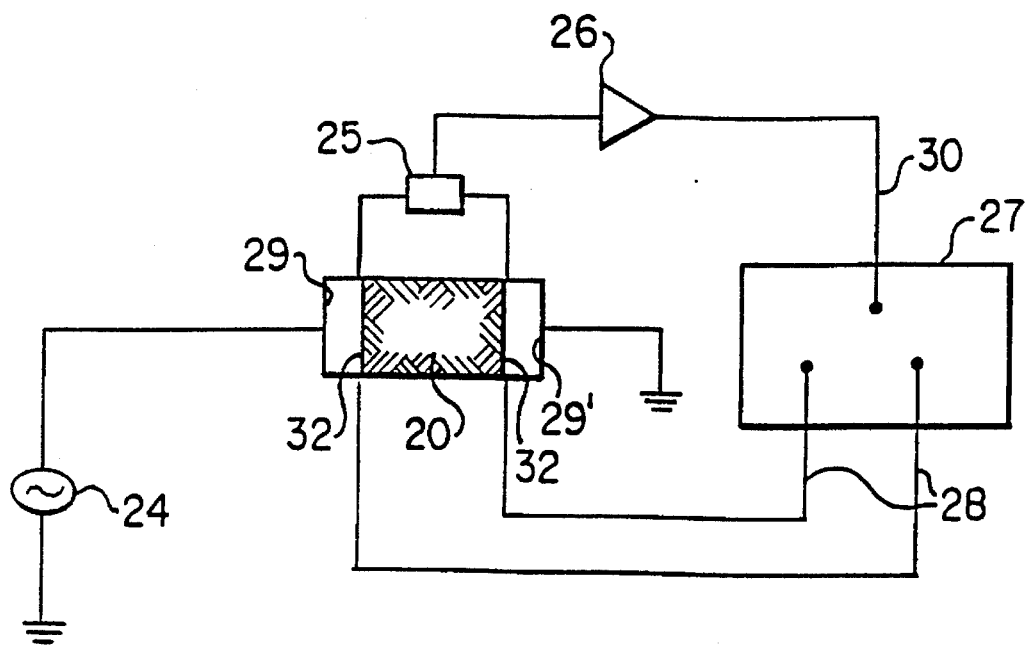
FIG. 2 is a simplified schematic showing an apparatus for measurement of induced electro-osmosis coefficient $K_2$ according to one embodiment of this invention.
Figure 3:
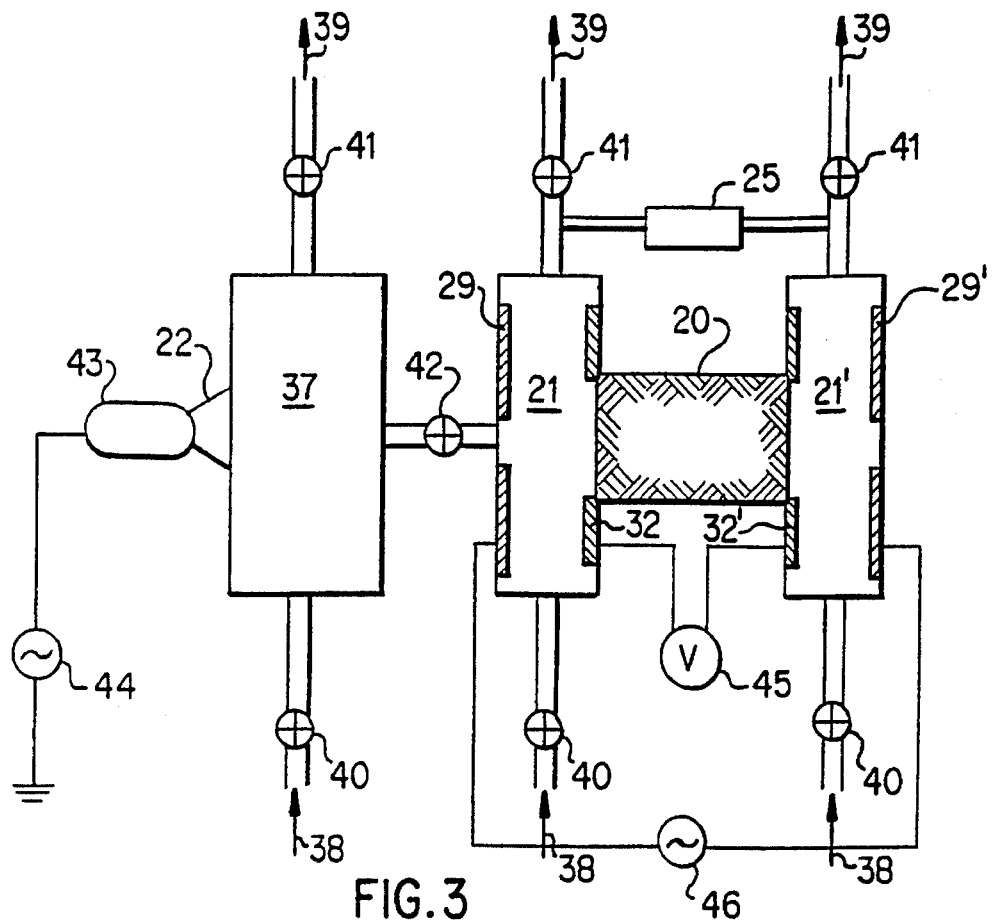
FIG. 3 is a simplified schematic showing a laboratory cell for measurement of streaming potential coefficient and electro-osmosis coefficient and conductivity according to one embodiment of this invention.

Using the apparatus shown in FIGS. 1–3, it has been found that the electro-osmosis signal, given by the ratio of the induced pressure to the applied voltage across the sample ($K_2 = P_e/V_a$), is a complex number which depends upon the angular frequency $\omega$ in the form of a Debye relaxation function, which may be expressed as:

$$K_2 = -Ae^{-i\phi} \qquad \text{Eq. 10}$$

wherein e is the base of natural logarithms, i is the imaginary unit $\sqrt{-1}$, A is amplitude of the electro-osmosis signal defined by $$A = K_2^o/(1+\omega^2\tau^2)^{1/2} \qquad \text{Eq. 11}$$

and $\phi$ is the phase angle of the electro-osmosis signal defined by the relationship $$\phi = \tan^{-1}(\omega\tau). \qquad \text{Eq. 12}$$

Figure 16:
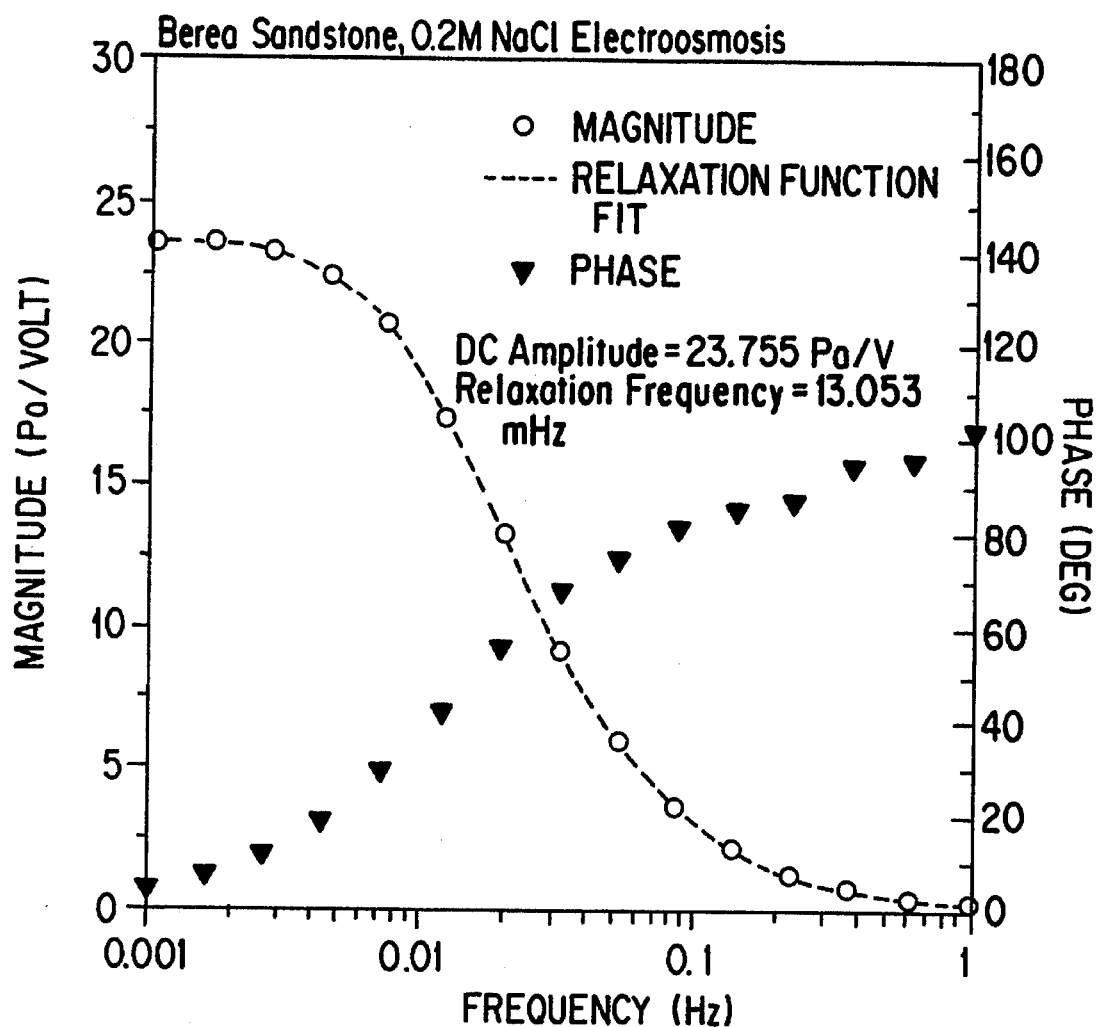
FIG. 16 shows the relationship of electro-osmosis signal amplitude and phase angle to frequency in measurement of a core sample of Berea sandstone according to one embodiment of this invention.

Here $K_2$ is as defined in Eq. 2 and $K_2^o$ is its d.c. absolute value, $\tau$ is a characteristic relaxation time, and $\phi$ goes from 90° to 0° as $\omega$ decreases toward zero. Defining $1/\tau = \omega_0$ as the angular relaxation frequency and $F_0 = \omega_0/2\pi$ as the relaxation frequency, when the measurement frequency f=$f_0$, Eq. 10 results in $A = K_2^o/\sqrt{2}$ and $\phi = 45°$. FIG. 16 shows an example of this behavior for a core sample of Berea sandstone saturated with 0.2M NaCl brine wherein y $f_0$ is about 0.013 Hz.

These relations allow determination of $K_2^o$ by measurements at any reasonable frequency such that $\phi$ is between 0° and 90°. Knowing the value of $\phi$ and the measurement angular frequency $\omega$, Eq. 12 can be used to determine the parameter $\tau$, or the product $\omega\tau$:

$$\omega\tau = \tan\phi \qquad \text{Eq. 13}$$

Since A is also measured, knowing $\omega\tau$ allows use of Eq. 11 to determine $K_2^o$ by the relation:

$$K_2^o = A(1+\omega^2\tau^2)^{1/2} = A(1+\tan^2\phi)^{1/2} \qquad \text{Eq. 14}$$

The process for measuring d.c. value of electro-osmosis coefficient $K_2^o$ of porous media formations containing fluid comprises: applying a.c. current at any finite frequency to the porous media, measuring electroosmosis in the porous media by measuring the relative amplitude A between the produced a.c. pressure and the applied a.c. voltage signals at the finite frequency applied using a differential pressure sensor and a pair of measurement electrodes near the application of the a.c. current, measuring the relative phase angle $\phi$ of the pressure and voltage signals by the pressure sensor and pair of measurement electrodes, and ascertaining $K_2^o$ by the relation $K_2^o = A(1+\tan^2\phi)^{1/2}$.

In this manner, the d.c. value $K_2^o$ is obtained by measuring A and $\phi$ at higher frequencies and the result used to estimate permeability according to Eq. 8, as previously.

Figure 17:
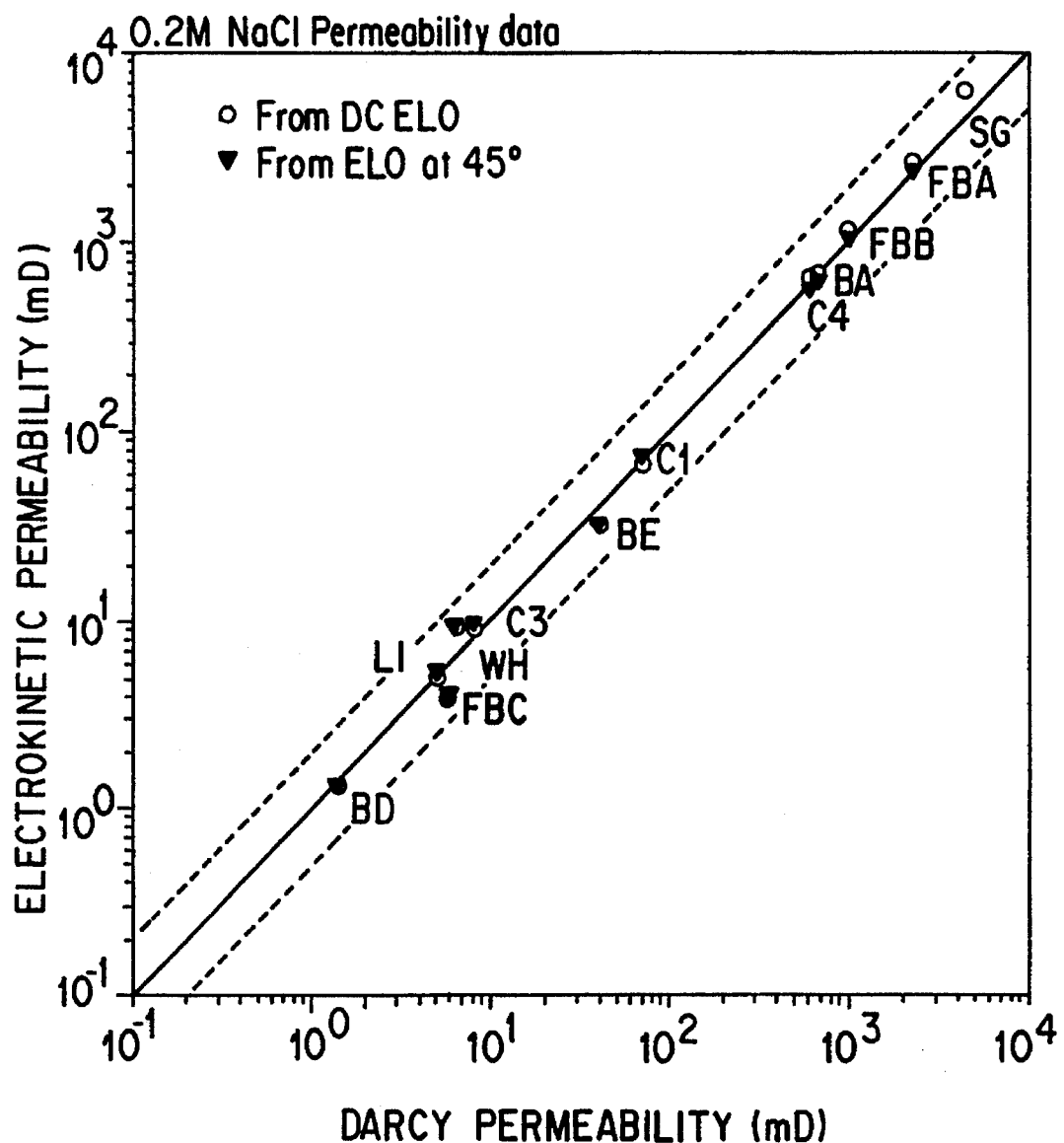
FIG. 17 shows that permeability calculated using electro-osmosis measurements at higher frequencies compare well with those made using much lower frequencies.

Making the measurement at higher frequency saves time and improves the signal-to-noise ratio. This is shown in FIG. 16 where one would have to make measurements at about 0.001 Hz to obtain a good estimate of the d.c value $K_2^o$. Instead, measurements may be made at 0.013 Hz with A=17 Pa/Volt and $\phi$=45°, so Eq. 13 results in $\phi\tau$=1. Then Eq. 14 results in $K_2^o=\sqrt{2}A$=24 Pa/Volt FIG. 17 shows that permeability calculated using this method to ascertain $K_2^o$ compares extremely well with using much lower frequencies.

Another method of ascertaining $K_2^o$ without using very low frequencies is to measure $K_2$ at several different frequencies and perform a least squares fit to Eq. 11 using $\tau$ and $K_2^o$ as two independent fitting parameters. According to this method, the process for determining d.c. value of electro-osmosis coefficient $K_2^o$ of porous media formations containing fluid comprises: applying a plurality of sets of a.c. current at different single angular frequencies $\omega$ to the porous media, measuring the relative amplitude A between each set of produced a.c. pressure and applied a.c. voltage signals of each said different single angular frequency using a differential pressure sensor and a pair of measurement electrodes near the application of the a.c. current, measuring the relative phase angle $\phi$ of the a.c. pressure and voltage signals at the pressure sensor and pair of measurement electrodes and ascertaining $K_2^o$ by performing a least squares fit to $A=K_2^o/(1+\omega^2\tau^2)^{1/2}$ using $\tau$ and $K_2^o$ as two independent fitting parameters.

Permeability may be obtained directly from the relaxation frequency without use of $K_1^o$ and $K_2^o$. The relaxation time $\tau$ results from a finite amount of liquid moving across the sample to produce a compression or decompression of the fluid chambers shown in FIGS. 3 and 4, thereby creating a pressure difference across the sample. In the apparatus, as shown in FIG. 3, if the sample and the fluid chambers have identical area $a_0$ and their lengths are $L_s$ and $L_f$, respectively, the relaxation frequency is:

where k is the permeability, $\eta$ is the fluid viscosity, and $\kappa$ is the fluid chamber compressibility. In any other geometry, k and $f_0$ will still be directly proportional to each other:

$$k=Cf_0 \qquad \text{Eq. 16}$$

where C is a constant depending only upon the cell geometry and fluid properties of viscosity $\eta$ and compressibility $\kappa$. C may be determined by making one measurement of $f_0$ on a sample of known permeability. Knowing C for a particular cell and fluid properties of viscosity $\eta$ and compressibility $\kappa$, measuring $f_0$ can be used to directly give permeability by Eq. 16. This process for determining permeability k of porous media formations containing fluid comprises: applying a.c. current at a single frequency f to the porous media, measuring the relative phase angle $\phi$ of the produced a.c. pressure and the applied a.c. voltage signal at the same frequency using a differential pressure sensor and a pair of measurement electrodes near the application of the a.c. current, determining the relaxation frequency $f_0$ using $f_0=f/\tan\phi$, and determining permeability k by the relation $k=Cf_0$ wherein C is a constant determined by making a measurement of $f_0$ using the same instrument on a sample of known permeability k. $f_0$ can be determined by one of the two methods outlined above:

Perform the measurement at a single frequency f, and knowing the phase angle $\phi$, $f_0$ can be obtained by $$f_0=f/\tan\phi \qquad \text{Eq. 17}$$

Figure 18:
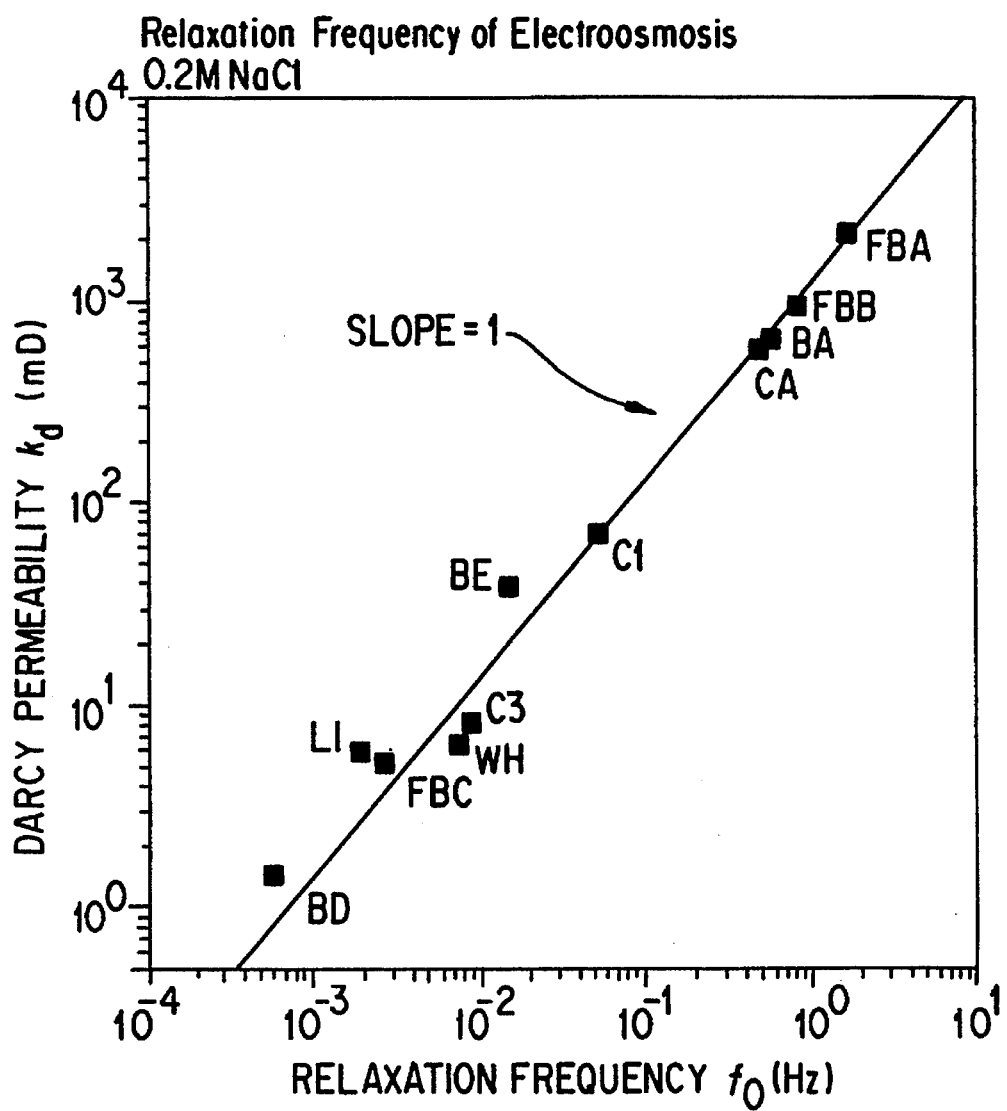
FIG. 18 shows the direct proportionality of permeability and electro-osmosis relaxation frequency observed with several rock and glass bead samples.

Perform multiple frequency measurements and perform a least squares fit of the amplitude A according to Eq. 11 with $\tau=1/(2\pi f_0)$. This process for determining permeability k of porous media containing fluid comprises: applying a plurality of sets of a.c. current at different angular frequencies $\omega$ to the porous media, measuring the relative amplitude A between each set of produced a.c. pressure and a.c. voltage signals at each different single angular frequency using a differential pressure sensor and a pair of measurement electrodes near the application of the a.c. current, determining the relaxation frequency $f_0$ by performing a least squares fit of the amplitude A according to $A=K_2^o/(1+\omega^2\tau^2)^{1/2}$ wherein $\tau=1/(2\pi f_0)$, and determining permeability k by the relation $k=Cf_0$ wherein C is a constant determined by making a measurement of $f_0$ using the same instrument on a sample of known permeability k. FIG. 18 shows the direct proportionality between k and $f_0$ observed in laboratory measurements on several rock and glass bead samples saturated with the same brine and mounted in the same cell. While $f_0$ was obtained by using multiple frequency measurements, measurements at a single frequency using Eq. 17 should be much more convenient when using a borehole apparatus.

Figure 9:
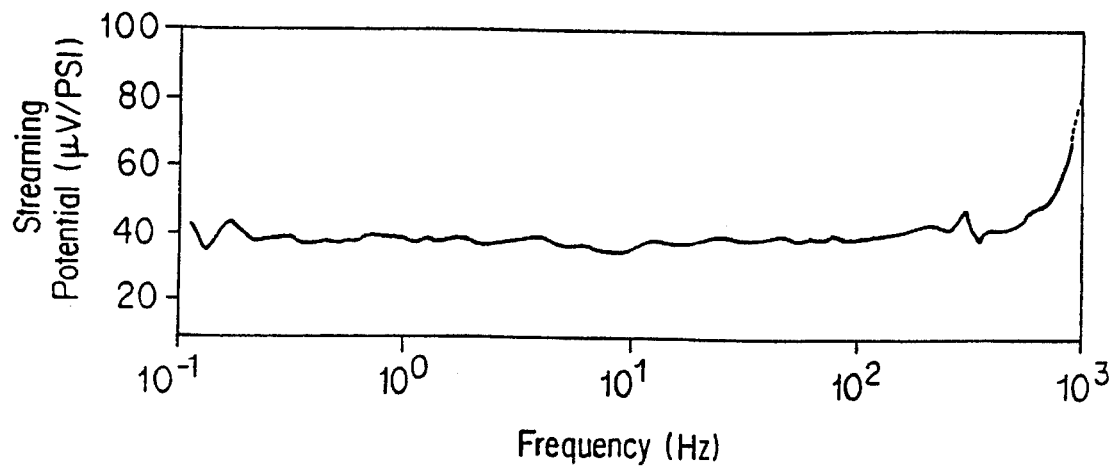
FIGS. 9 and 11 show measurement of magnitude of induced streaming potential coefficient $K_1$ according to one embodiment of this invention.
Figure 11:
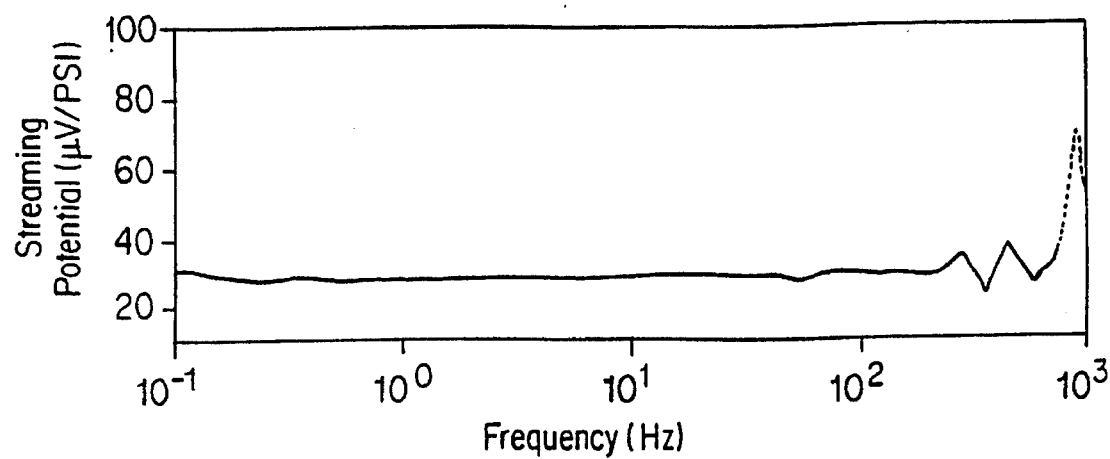

FIGS. 9 and 11 show that the streaming potential (STP) signal was independent of frequency below about 100 Hz for homogeneous materials, in other words, $K_1=K_1^o$ below 100 Hz. The reason is that since STP is a ratio of the voltage difference $V_s$ and pressure difference $P_a$ across the sample, it does not matter how the voltage and pressure vary along the sample. When a pressure is applied at one end of the sample for a brief duration, only the fluid at that end of the sample is compressed. However, if the pressure is maintained for a longer period of time, an approximately linear decrease in pressure would develop between opposite ends of the sample. The pressure gradient and the voltage gradient for the two situations are different, but the end-to-end values of $V_s$ and $P_a$ are the same, but, only in homogeneous samples. In a borehole, a mudcake covers the borehole wall. In this case, when a pressure is applied for a short duration, the pressure drop occurs only in the thin mudcake layer. When a pressure is applied for a longer duration, the pressure drop is across the mudcake and the rock formation connected in series. The STP signal for these two cases is different. In Eq. 3, $K_1^o=\epsilon\zeta/4\pi\eta\sigma_W$, $\epsilon,\eta$ and $\sigma_W$ are properties of the fluid, dielectric permittivity, viscosity, and brine conductivity, respectively, and may be presumed to be the same for the mudcake and the rock. However, $\eta$ is the surface potential which is generally different for the mudcake than for the rock. Thus $K_1$ must change as a function of frequency. At high frequencies, the pressure drop occurs entirely in the mudcake and the signal is characteristic of properties of the mudcake. At low frequencies, the pressure drop occurs in both the mudcake and the rock and the signal is characteristic of combined properties of the mudcake and the rock. A characteristic frequency $f_s$ marks the maximal change with respect to frequency between these two limiting values. In frequency ranges below about 1 kHz, the pressure in the fluid propagates according to the diffusion equation such that in time t the pressure gradient penetrates a distance L according to the equation $$L^2=Dt \qquad \text{Eq. 18}$$

where D is a diffusion constant. In the mudcake where the solid matrix frame is much more compressible than the fluid, the diffusion constant of the mudcake $D_{cake}$ may be expressed:

$$D_{cake}=k_{cake}K_{cake}/\eta \qquad \text{Eq. 19}$$

where $k_{cake}$ and $K_{cake}$ are the permeability and bulk modulus, respectively, of the mudcake. The relevant diffusion constant is that of the mudcake $D_{cake}$ and not that of the rock $D_{rock}$. Substituting Eq. 19 into Eq. 18 with $t=1/\omega=1/2\pi f_s$, one obtains the penetration distance at $f_s$:

$$L^2 = D_{cake}/2\pi f_s \qquad \text{Eq. 20}$$

Thus, by performing the streaming potential measurement over a range of frequencies, $f_s$ can be determined which can be used to determine the thickness of the mudcake if the elastic properties of the cake is known or ascertained by another acoustic logging technique. Conversely, if the mudcake thickness is known by other means, the bulk modulus of the cake may be determined. Even if the diffusion constant of the mudcake is entirely unknown, comparison of $f_s$ at different locations in the borehole would indicate relative thicknesses of the mudcake. Monitoring changes in $f_s$ with time indicates the buildup of the mudcake as a function of time. The process for determination of the thickness of mudcake lining a borehole comprises: applying a plurality of sets of pressure oscillations at different frequencies to fluid in the mudcake, measuring induced a.c. STP voltage signal $V_s$ at each of the different frequencies of pressure oscillation using a pair of measurement electrodes near the application of the pressure, measuring differential fluid pressure $P_a$ in the porous media between the electrodes, determining characteristic frequency $f_s$ at the change between these two values, determining $K_1$ by the relation $V_s/P_a$, determining the thickness of said mudcake adjacent the application of pressure oscillations by determining the penetration distance L by the relation $L^2=D_{mudcake}/2\pi f_s$ wherein $D_{mudcake}$ is the pressure diffusion constant of the mudcake.

Figure 19:
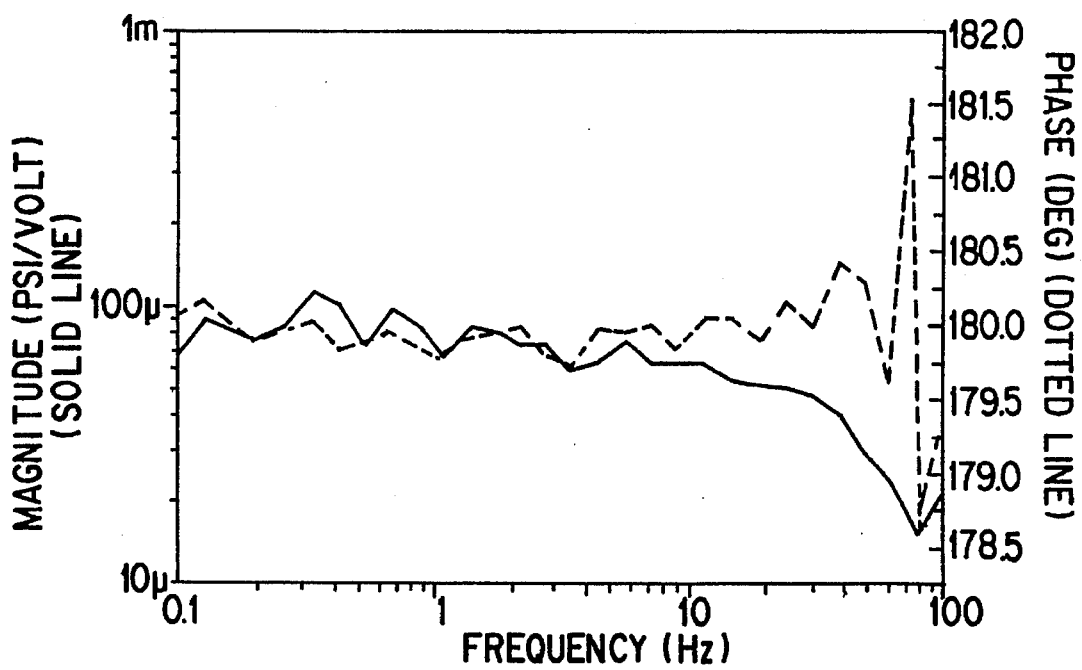
FIGS. 19–20 show streaming potential signal amplitude and phase angle obtained from a layered sample of glass beads and rock over a range of frequencies.
Figure 20:
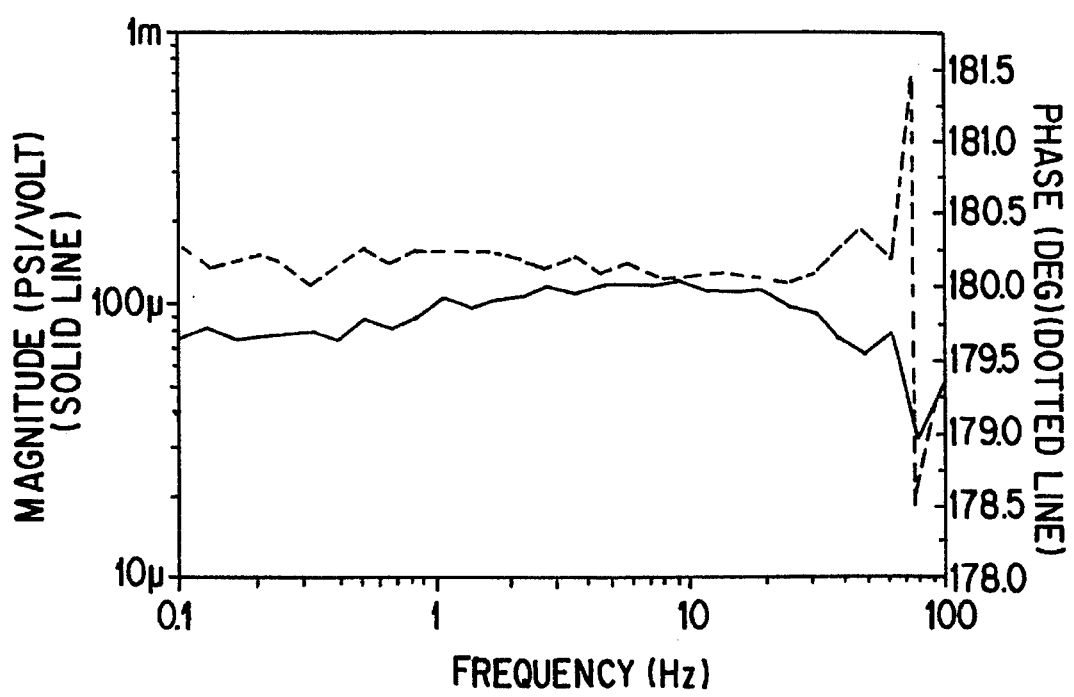

To illustrate the effectiveness of the above-described technique, a porous rock sample was joined to a layer of glass beads and streaming potential measurements made over a range of frequencies of 0.1 to 100 Hz. Results obtained by applying pressure on the rock side are shown in FIG. 19 and by applying pressure on the glass bead side are shown in FIG. 20. It is seen that at a high frequency, 10 Hz, the signal is about 60 µV/psi when the pressure is applied to the rock side and about 120 µV/psi when the pressure is applied to the glass bead side. This difference is due to the pressure gradient having penetrated only part of the sample adjacent to the transducer, rock in the first case and glass beads in the second case. At a low frequency of about 0.1 Hz, both cases result in a signal of about 80 µV/psi, resulting from the pressure gradient having penetrated both sections of the sample. In this case, the combined effect of the glass beads and the rock is measured and it does not make any difference to which side the pressure is applied. In the results shown in FIGS. 19–20, the characteristic frequency is about 1 Hz. It is evident that this technique can be used to detect the thickness of layers of any layered porous material, in addition to mudcake and rock. The process for determination of the thickness of layered porous media formations containing fluid comprises: applying a plurality of sets of pressure oscillations at different frequencies to fluid in the porous media, measuring induced a.c. streaming potential voltage signal $V_s$ at each of the different frequencies of pressure oscillation using a pair of measurement electrodes near the application of the pressure, measuring differential fluid pressure $P_a$ in the porous media between the electrodes, determining $K_1$ by the relation $V_s/P_a$, determining characteristic frequency $f_s$ at the maximal change of $K_1$ with respect to frequency between the two limiting values, determining the thickness of the layer adjacent the application of pressure oscillations by determining the penetration distance L by the relation $L^2=D_{adjacent\ medium}/2\pi f_s$ wherein $D_{adjacent\ medium}$ is the pressure diffusion constant of the medium adjacent to the pressure source.

By contrast, the teachings of U.S. Pat. No. 4,427,944 propose using the relationship that in the rock formation, if it is assumed that the solid rock matrix frame is much less compressible than the fluid, then $D_{rock} \sim k_{rock} K_{fluid}/\eta\phi$ where $k_{rock}$ is the rock permeability, $K_{fluid}$ is the bulk modulus of the fluid, and $\phi$ is the porosity of the rock. If the solid rock matrix frame is compressible, $K_{fluid}$ in this equation would be replaced by some effective value. U.S. Pat. No. 4,427,944 proposes to measure the pressure propagation time over a fixed distance L set by the spacing between the electrodes and use Equation 18 with the above relation to determine rock permeability. However, this does not account for the fact that the pressure source and the electrodes are in contact with the mudcake which alters the propagation time. Further, U.S. Pat. No. 4,427,944 proposes to measure the streaming potential signal as a function of time, while the method of the present invention measures it as a function of frequency. The frequency domain measurement provides higher signal to noise ratio through use of the lock-in technique. Also, the high and low frequency limits of the straming potential values can be clearly identified using the frequency domain measurement.

A simplified schematic of a laboratory apparatus for measurement of streaming potential by the a.c. method is shown in FIG. 1. Power is supplied to oscillator 24 which supplies an oscillating voltage through power amplifier 23 to electro-mechanical transducer 22 to produce pressure oscillations at a frequency of about 0.001 to about 1000 Hz in the fluid in fluid compartment 21. Suitable pressures are low, in the order of about 0.1 to about 10 psi are suitable, preferably about 1 to about 10 psi. Porous material, such as rock 20, is in sealed relation between the fluid in fluid compartment 21 on one side and the fluid in fluid compartment 21' on the opposite side so that the only fluid communication between opposite sides is through rock 20. The differential pressure of the fluid on opposite sides of rock 20 is measured by differential pressure sensor 25 which may be a piezoresistive or piezoelectric transducer, having the ability to measure the pressure with $10^{-6}$ psi resolution. This sensor provides a small voltage output which is amplified by preamplifier 26 and undergoes A/D conversion to give a pressure reading. Voltage electrodes 32, such as chloridized silver, are used to detect the induced voltage across rock 20 and provide it through differential voltage input 28 to lock-in amplifier or frequency response analyzer 27 for measurement at the prescribed frequency of the applied pressure oscillations resulting in obtaining both phase and amplitude of the voltage signals below 1 µV without d.c. interference. The a.c. pressure can be applied by an electromechanical transducer such as similar to an audio speaker or a rotating cam shaft similar to an automobile distributor shaft or a solenoid drive, or any other suitable means to result in alternating pressure oscillations over a wide range of frequencies, such as, 1 mHz to 1 kHz. A stripped audio speaker has been found satisfactory. With the description and reference to FIG. 1, one skilled in the art will know various types of specific components to appropriately use in the apparatus for measurement of a.c. induced voltage and pressure differential according to this invention. This apparatus induces an a.c. voltage due to streaming potential across the measurement sample which is measured near the source of and at the finite frequency of the applied pressure oscillations from which streaming potential coefficient $K_1$ may be obtained by application of Eq. 1.

A simplified schematic of the apparatus for measurement of electro-osmosis by the a.c. method is shown in FIG. 2. The apparatus is very similar to that shown in FIG. 1, except oscillator 24 supplies an oscillating voltage to current electrode 29 which drives alternating current through sample 20 inducing electro-osmotic pressure difference across rock 20 which is detected at the finite frequency of applied voltage in the same manner as described with respect to the streaming potential measurement. Also, in the same manner as described with respect to streaming potential, the differential fluid pressure on opposite sides of rock 20 is measured by differential pressure sensor 25. In order to maximize the pressure oscillations in the electro-osmosis measurements, the fluid chambers on each side of the rock sample should be maintained as small and as rigid as practical. With the above description and reference to FIG. 2, one skilled in the art will know various types of specific components to appropriately use in the apparatus for measurement of a.c. electro-osmotic induced pressure and applied voltage differential. This apparatus induces a.c. pressure due to electro-osmosis in rock which is measured near the source of and at the finite frequency of the applied a.c. voltage from which electro-osmotic coefficient $K_2$ may be obtained by application of Eq. 2.

FIG. 3 is a simplified schematic showing of a laboratory cell design for measurement of streaming potential and electro-osmotic coefficients and conductivity across a core sample of rock according to this invention. The cell has fluid chambers 21 and 21' on either side of rock sample 20 and fluid chamber 37 adjacent electromechanical transducer 22. Each of the fluid chambers has a fluid inlet 38 and fluid outlet 39 controlled by inlet valves 40 and outlet valves 41, respectively, to fill the chambers with fluid and to flush out any air bubbles. Each of fluid chambers 21 and 21' have a set of current electrodes 29 and a set of voltage electrodes 32. With rock sample 20 between fluid chamber 21 and fluid chamber 21', the conductivity is simply measured by applying an a.c. current and measuring the voltage across the sample. Application of the a.c. current and measurement of the voltage are performed at the same finite frequency, between about 1 mHz and 1 kHz. Differential pressure sensor 25 is in fluid communication with fluid compartments 21 and 21' to simultaneously detect pressure differences from which the electro-osmotic coefficient $K_2$ may be calculated. While these measurements are being made, isolation valve 22 connecting fluid chamber 37 with fluid chamber 21 is kept closed. To perform a streaming potential measurement, isolation valve 42 is open and oscillating pressure is applied to the fluid in fluid chamber 37 by electromechanical transducer 22 driven by electromechanical drive 43 powered by power source 44. Pressure oscillations are transmitted through valve 42 to the fluid in fluid compartment 21 and thus to porous rock sample 20. The differential pressure and voltage across sample 20 are measured by the same sets of pressure sensors and electrodes, respectively, as used in the electro-osmosis measurement, and used to calculate the streaming potential coefficient $K_1$. It should be noted that all measurements are made in close proximity to each other and that while the sample is maintained under fluid pressure flowing fluid disturbances are not encountered.

Figure 4:
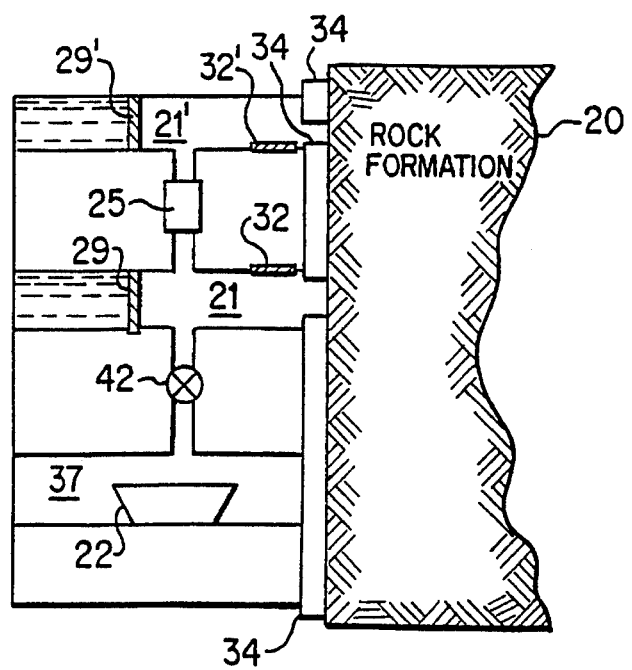
FIG. 4 is a simplified schematic showing a down-the-hole apparatus for simultaneous measurement of sub-surface rock formation conductivity and streaming potential and electro-osmosis coefficients according to one embodiment of this invention.

FIG. 4 shows in simplified schematic fashion a tool pad design for in-situ down the hole subterranean porous media measurement of streaming potential and electro-osmosis coefficients by a.c. methods of this invention and measurement of conductivity of the porous media. The apparatus is pressed against rock 20 with pad seals 34 isolating fluid chamber 21 from fluid chamber 21' and isolating all of the fluid chambers of the tool pad from the surrounding fluid and fluid flow. Current electrodes 29 and 29' and voltage electrodes 32 and 32' are situated in fluid chambers 21 and 21', respectively. Isolation valve 42 separates fluid chamber 21 from fluid chamber 37 which houses electromechanical transducer 22. For electro-osmosis and conductivity measurements, isolation valve 42 is closed and voltage electrodes 32 and 32', measure the voltage difference between them when a current is passed through the rock determining the conductivity while simultaneously the induced pressure difference is detected by differential pressure sensor 25, from which the electro-osmosis coefficient $K_2$ may be calculated. For streaming potential coefficient measurements, isolation valve 42 is opened and an oscillating pressure applied by electromechanical transducer 22 is applied to the rock formation through fluid chamber 21. The induced voltage and pressure differential in the rock between fluid chambers 21 and 21' is measured by voltage electrodes 32 and 32' and pressure sensor 25, respectively. It is desired that fluid chamber volumes 21 and 21' are small and as rigid as possible to maximize the pressure differential. Suitable electronics for powering the transducer and current electrodes as well as for measurement of the induced voltages and pressure differential may be provided in any manner as recognized by one skilled in the art, especially after reading the above description with respect to FIGS. 1 and 2. The apparatus for in-situ down the hole determination of permeability k of porous rock formation containing fluid providing reduced effect of mudcake lining a borehole wall comprises: chamber walls forming a plurality of four and greater adjacent chambers comprising a first end chamber, a second opposite end chamber, and at least two inner chambers between the first end and the second end chambers, each chamber having an opening on one side adjacent the mudcake of the porous rock formation; sealing means around each opening capable of forming a generally fluid-tight seal with a face of the mudcake of the porous rock formation thereby isolating each fluid chamber from fluid communication with each other except through the mudcake and porous rock formation; means for applying pressure oscillations at a finite frequency through fluid in the first and second end chambers to fluid in the porous rock formation in a streaming potential mode of operation, the differential pressure between the end chambers being monotonic and the two pressure sources operated 180° out-of-phase; electrode means in the first and second end chambers for applying a.c. current at a finite frequency between the end chambers through fluid in the porous rock formation in an electro-osmosis mode of operation; measurement electrodes located in each of the end chambers and inner chambers for sensing induced differential a.c. voltage signal between each pair of chambers at the finite frequency of the applied pressure oscillations in streaming potential mode and capable of measuring electro-osmosis a.c. applied voltage signal in electro-osmosis mode; and fluid pressure sensing means between each pair of adjacent chambers for sensing and measuring differential fluid pressure between each pair of chambers.

In the in-situ subterranean formation measurements according to this invention, the streaming potential and electro-osmotic induced voltages are separately measured by both electrodes located near the application of pressure oscillations and alternating voltage, respectively, as compared to prior art measurements which were made at a location spaced from the application source, such as one electrode down the hole and the other at the ground surface. The embodiments shown in FIGS. 3 and 4 have the advantage that the streaming potential and the electro-osmosis measurements can be made separately to minimize interference and maximize the signal to noise ratio, or if signal level is not a problem, may be made together to provide savings of time. Also, the application and measurement electrodes are isolated from fluid flow which may cause significant interference. In each case, the apparatus and process of this invention contemplates measurement of differential pressure as well as voltage induced in the formation between points of application and detection, which are in proximity to each other and isolated from fluid flow. The distance between application and measurement should be one wave length and less that of the sound wave propagated by the application of pressure or the wave propagated by the application of a.c. current. In preferred embodiments, the distance between application and measurement is less than one tenth of the wave length of applied oscillation pressure or a.c. current.

Figure 21:
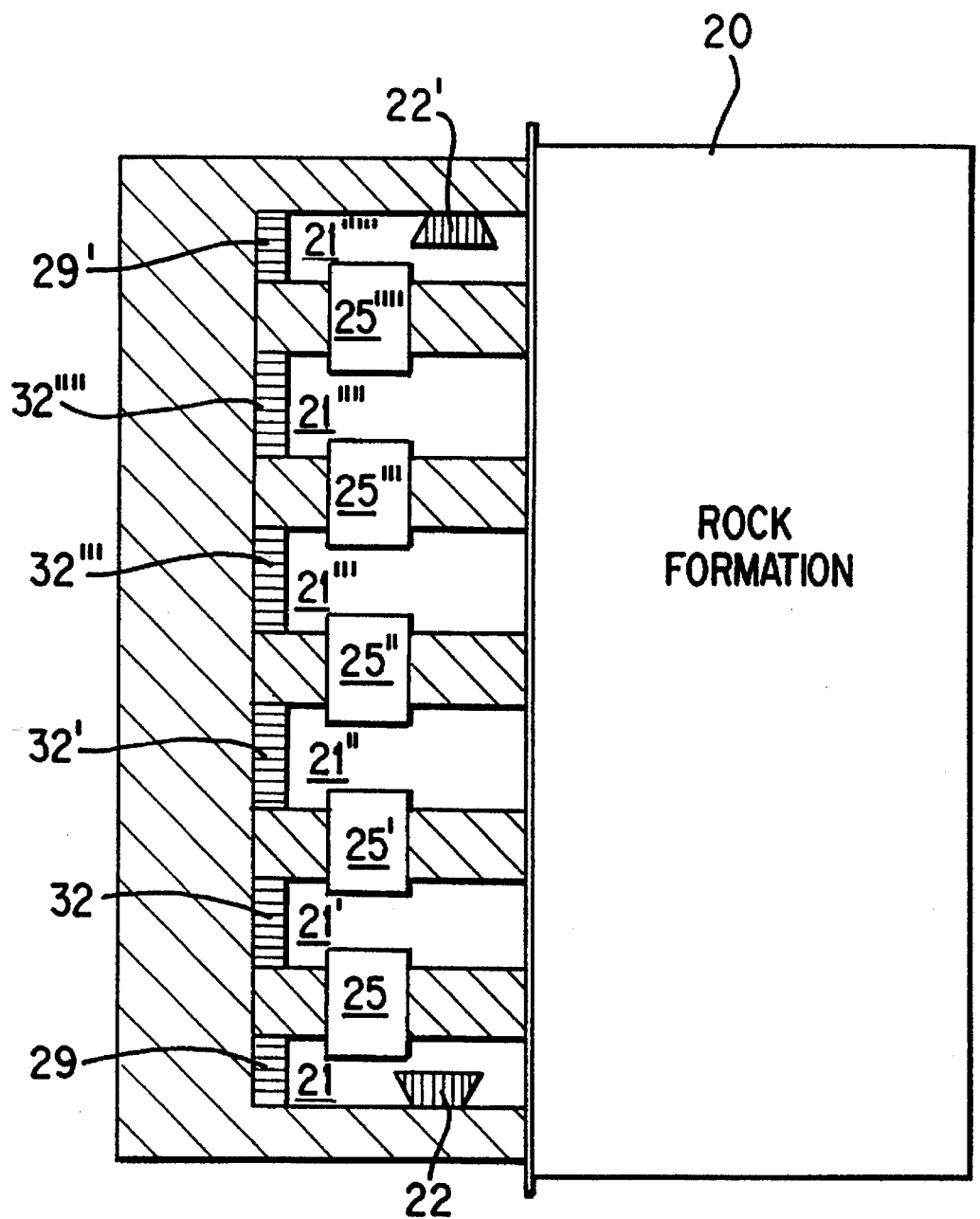
FIG. 21 is a simplified schematic showing a down-the-hole apparatus having a plurality of detection electrodes and chambers according to one embodiment of this invention.

Erroneous permeability measurements due to the effect of mudcake in the borehole can be reduced or eliminated by use of a pad-tool having multiple detection cavities. FIG. 4, as described above, shows a tool pad design in which measurements of differential pressure and voltage are made between adjacent fluid chambers 21 and 21'. To correct for the effect due to the mudcake, FIG. 21 in simplified schematic fashion shows a tool pad design having additional fluid chambers 21", 21''', 21'''' and 21''''' for detection of voltage and pressure differences between each adjacent pair $(V_1P_1)$, $(V_2P_2)$, $(V_3P_3)$, etc. As shown in FIG. 21, electrodes 29 and 29' in end fluid chambers 21 and 21''''', respectively, are used for both injecting current and measuring voltage. Voltage electrodes 32, 32', 32'', 32''' and 32'''' are used only for measuring voltage. Differential voltages $V_1$, $V_2$, etc., are determined from measurements between any of the neighboring electrode pairs. Pressure sources 22 and 22', such as electromechanical transducers, are placed in the end fluid chambers and can be operated 180° out of phase to form a push-pull pair to maximize the pressure differential. The frequency of the pressure oscillations should be low enough so that the pressure variation between the two end chambers is monotonic. The differential pressure between adjacent chambers, $P_1$, $P_2$, etc., can be determined by measurements using pressure sensors 25, 25', etc., respectively The streaming potential coefficient $K_1$ can he calculated from any of the pairs: $V_1/P_1$, $V_2/P_2$, etc., respectively. At any measurement frequency, the pressure signal only penetrates a distance L given by Eq. 18. Therefore, the chamber pairs furthest from the pressure source may not detect any signal, while the chamber pair closest to the pressure source will always have the largest signal. The strength of the signal falls off with increasing distance. In contrast to the teachings of U.S. Pat. No. 3,599,085 which measures the decay length, this invention uses two pressure sources operated out of phase making the pressure drop more evenly distributed. By comparing the near-field value and far-field value of $K_1$, the mudcake effect can he distinguished. Specifically, signals between fluid chambers 21 and 21' and those between 21'''' and 21''''' result from fluid flowing through the mudcake and rock in series since the compression generated by the pressure source must first penetrate the mudcake before propagating into the rock formation. All other chamber pairs, in the central portion, sense the effect of the mudcake in parallel with the rock formation. Since the mudcake is thin, it represents a high resistance path and the predominant flow is in the rock formation. Therefore, detecting the voltage and pressure differences between two central fluid chambers, such as 21'' and 21''', largely removes the effect due to the mudcake. The process having reduced effect of mudcake on a borehole wall in measuring streaming potential coefficient $K_1$ of porous rock formations containing fluid comprises: applying pressure oscillations at a finite frequency to the fluid from chambers at opposite ends of a plurality of adjacent chambers, measuring induced a.c. voltage signal $V_s$ at the finite frequency using a pair of measurement electrodes in two adjacent interior chambers spaced from the chambers at opposite ends, measuring differential fluid pressure $P_a$ in the porous rock formation by differential pressure sensors in two adjacent interior chambers, and ascertaining $K_1$ by the relation $K_1 = V_s/P_a$ wherein $V_s$ is the measured a.c. streaming potential voltage signal and $P_a$ is the measured applied pressure differential.

The invention will be described with respect to specific examples using specific apparatus components and measurement conditions which are exemplary and should not be considered to limit the invention in any way.

EXAMPLE I (Comparative)

Streaming potential was measured by application of constant pressure of various amounts, as indicated in FIGS. 5 to 8, with measurement of induced voltage across the sample as shown in FIGS. 5 to 8. The d.c. data shown in FIGS. 5 to 8 were obtained using an apparatus similar to that shown in FIG. 1 except that pressure difference across the cell was generated by a syringe pump attached to fluid chamber 21 with injection of fluid at a constant flow rate. The pressure difference was sensed by the same differential pressure sensor 25, but its output was fed to a d.c. digital voltmeter. In other words, the a.c. driver and detection circuits described with respect to FIG. 1 were replaced by their d.c. counterparts.

Figure 5:
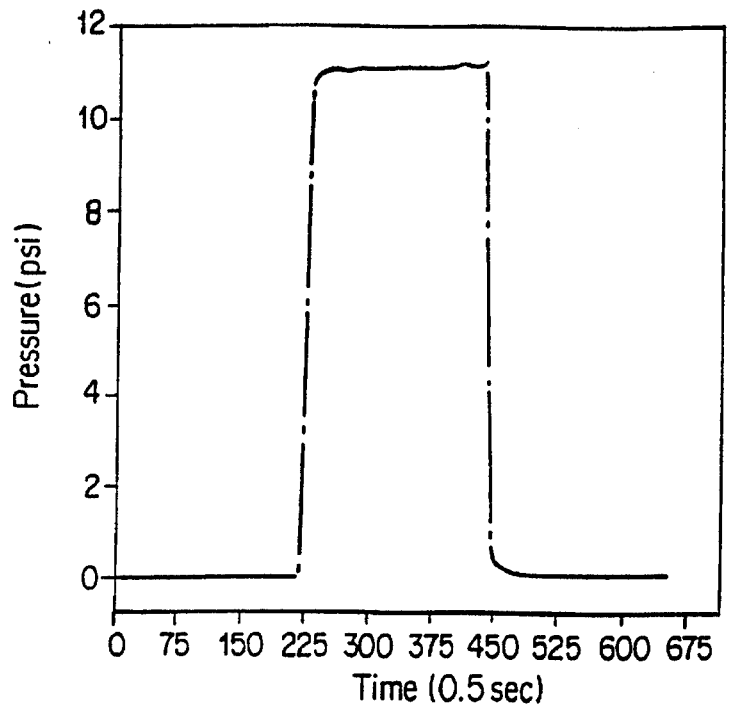
FIGS. 5 and 7 show measurement of pressure differential according to prior art methods.
Figure 6:
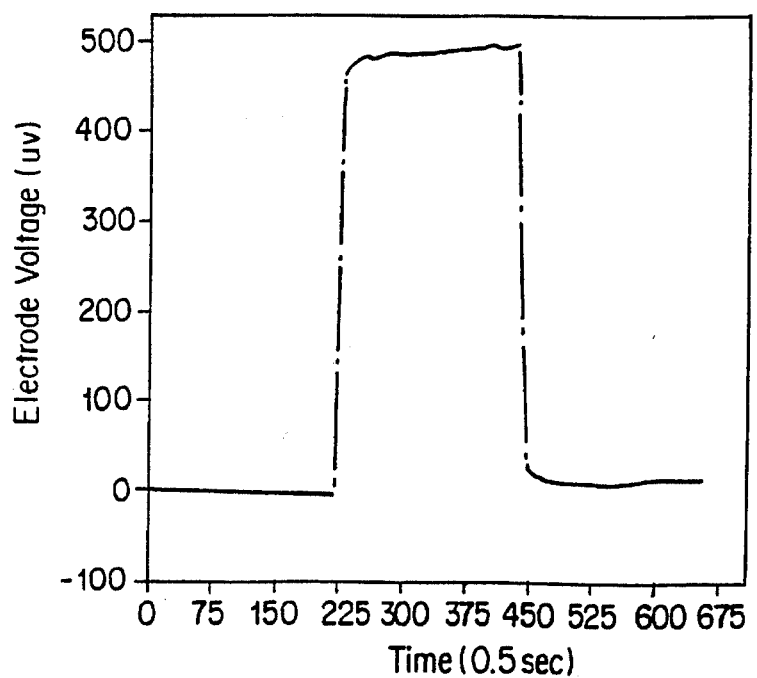
FIGS. 6 and 8 show measurement of induced streaming potential voltage according to prior art methods.

One test using Berea-A sandstone having a porosity of 0.229 and formation factor of 11.2 was performed in 0.26M NaCl at a flow rate of 25 ml/min. FIGS. 5–6 show results of a 2 minute idle and 2 minute constant flow rate injection. One can observe change in pressure results in a corresponding step change in induced voltage, so that streaming potential can be easily obtained.

Figure 7:
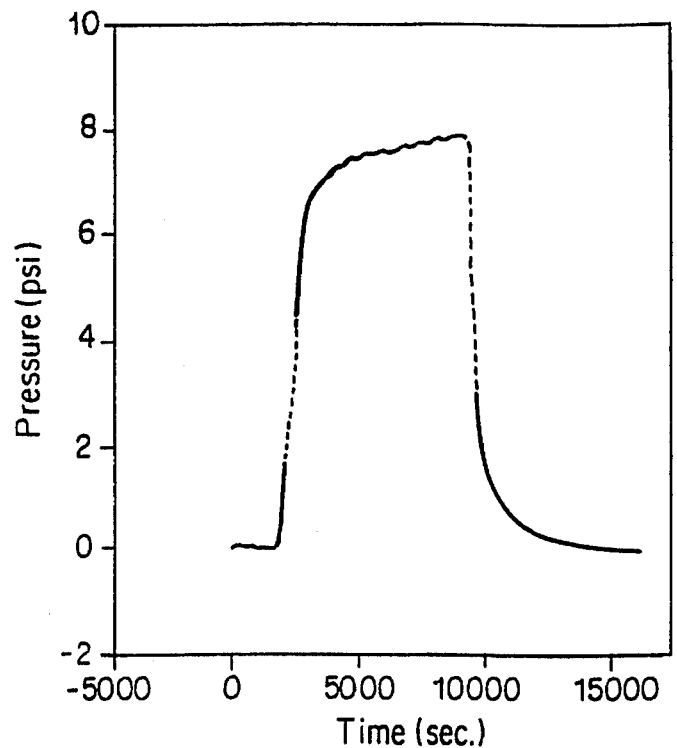
Figure 8:
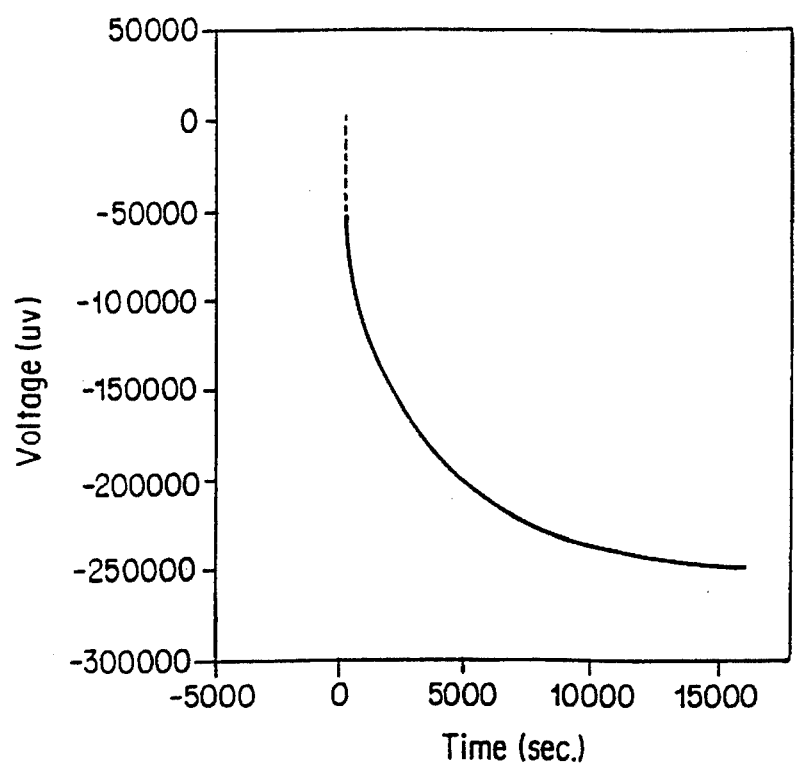

A second test using more shaly Bandera sandstone having a porosity of 0.219 and formation factor 16.9 was performed in 0.26M NaCl at a flow rate of 0.06 ml/min. using the same apparatus and procedure as above. The much lower flow rate was a result of low permeability of the sample of about 1 milli darcy. FIGS. 7–8 show results of a 30 minute blank and 120 minute sample run in which an observed step change in pressure did not result in a measurable step change in induced voltage, due to the electrodes having a larger background interfacial voltage that drifted as a function of time. This demonstrates the failure of the method of application of constant flow rate and measurement of induced d.c. voltage for determination of streaming potential when using low permeability porous media. We have found from laboratory measurements that both d.c. and a.c. methods may be used to obtain streaming potential and electro-osmosis measurements which are in good agreement with each other for sample permeabilities above about 10 milli-darcies. The Berea A sample has k equal to about 650 mD and the Bandera sample has k equal to about 2 mD. For samples having permeabilities lower than about 10 milli-darcies, only the a.c. measurement technique of this invention has been found to be successful.

EXAMPLE II

Figure 10:
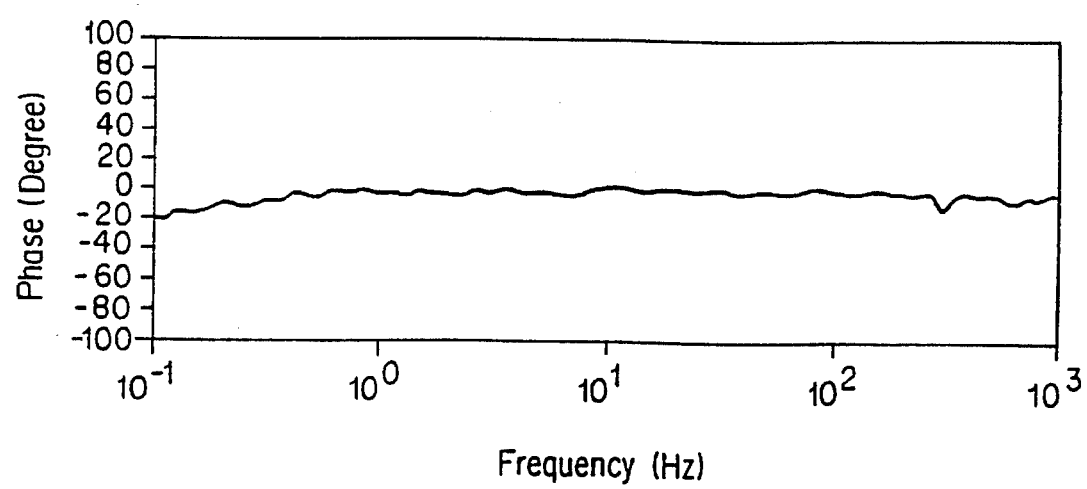
FIGS. 10 and 12 show measurement of phase of induced streaming potential coefficient $K_1$ according to one embodiment of this invention.
Figure 12:
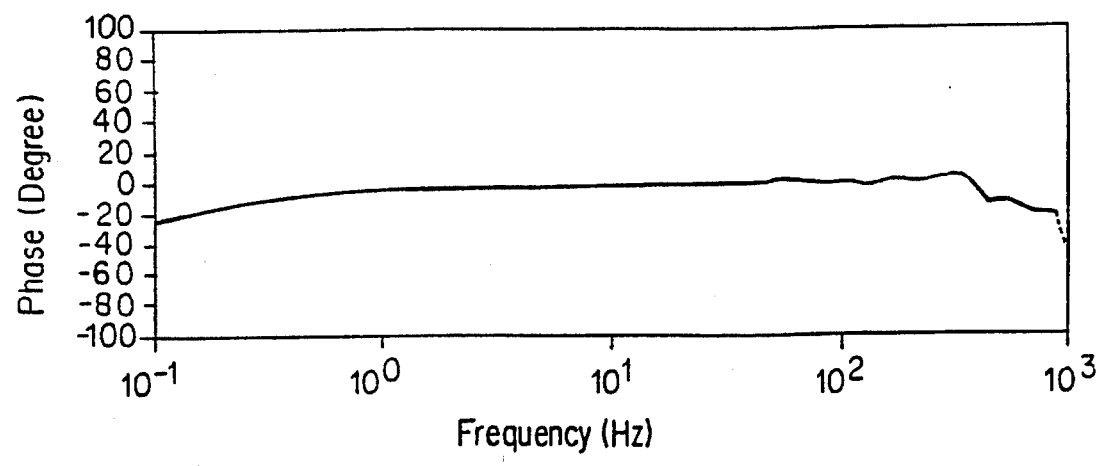

Using an apparatus as shown in FIG. 1, and described above, samples of the same Berea sandstone and Bandera sandstone as measured in Ex. I, were evaluated by application of pressure oscillations at a finite frequency and measurement of induced streaming potential voltage at that frequency and pressure differential according to the present invention. The streaming potential coefficient $K_1$ may then be obtained by application of Eq. 1. The measurements were conducted in 0.26M NaCl with application of pressure oscillations of 1 psi at frequencies of 0.1 to 1000 Hz. The a.c. pressure was generated by a modified audio speaker driven by a power amplifier in the 0.1 to 1000 Hz frequency range. The resulting pressure oscillation and a.c. streaming potential signals were fed to a pair of preamplifiers and the relative amplitude and phase of their outputs were compared by a digital frequency response analyzer. FIGS. 9–10 show resulting magnitude and phase angle of the streaming potential coefficient for Berea sandstone and FIGS. 11–12 show the corresponding values for Bandera sandstone. It is observed that for the Berea sandstone the streaming potential coefficient between 0.1 and 1.0 Hz is substantially constant and in good agreement with the value obtained in Example I by the constant pressure application method. However, for the Bandera sandstone which was not measurable by the constant pressure application method of Ex. 1, application of pressure oscillations and measurement of streaming potential coefficient at the same frequency resulted in good magnitude and phase angle measurements, as shown in FIGS. 11–12.

EXAMPLE III

Further measurements were conducted as described in Example II on additional rock formations to determine streaming potential coefficient with the oscillating pressure application and measurement of a.c. induced voltage at the same frequency of the pressure application according to the present invention. The results are summarized in Table 1.

Figure 13:
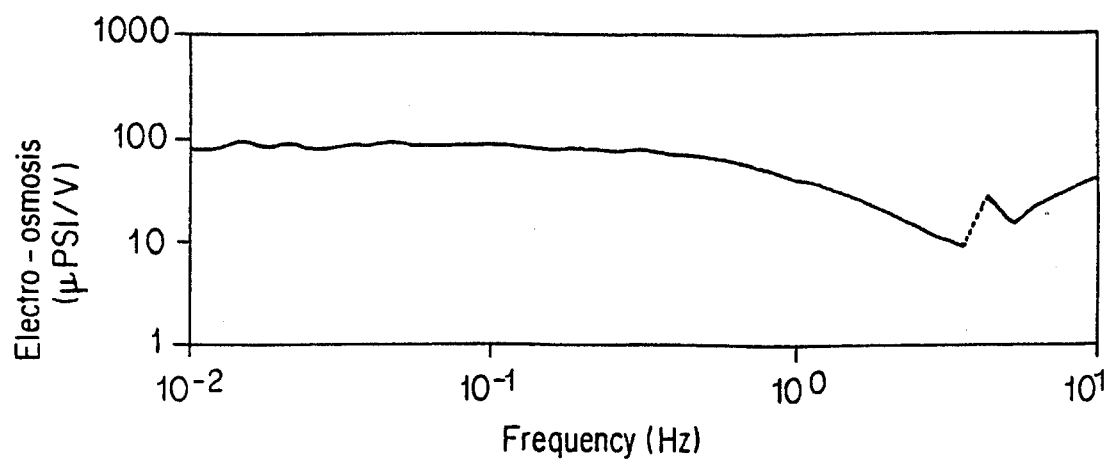
FIG. 13 shows measurement of magnitude of electro-osmosis coefficient $K_2$ according to one embodiment of this invention.
Figure 14:
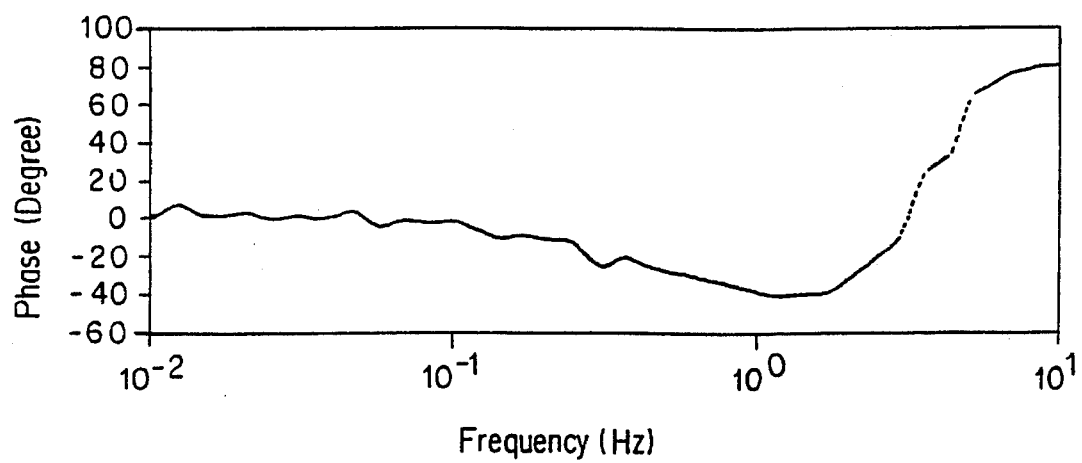
FIG. 14 shows measurement of the phase angle of electro-osmosis coefficient $K_2$ according to one embodiment of this invention.

The same rock formations were used to determine electro-osmosis coefficient $K_2$ using an apparatus as shown in FIG. 2 by application of a.c. voltage at finite frequency and measurement at the same frequency of induced electro-osmotic pressure signals which are fed to two preamplifiers and then compared by a digital frequency response analyzer and pressure differential according to the present invention. The fluid used was 0.26M sodium chloride solution. The electro-osmotic coefficient $K_2$ may then be obtained by application of Eq. 2. The results are summarized in Table 1. FIGS. 13 and 14 show magnitude and phase angle, respectively, of $K_2$ for FountainBleau sandstone between 0.01 and 10 Hz.

Fused glass bead samples were used as standards because they are rigid in the sense that the structure is not changed by the fluid flowing through the pores. Data for the glass bead samples was obtained in the same fashion except that. the fluid used was 0.1M sodium chloride solution. The results are summarized in Table 1.

TABLE 1

| Rock Descript. | Poros. | Form. Fact. | Stream. Potent. ($\mu$V/PSI) | $\zeta$-potent. (mV) | Electro-osmosis (mPSI/V) | Permeability (mDarcy) | |
|---|---|---|---|---|---|---|---|
| | | | | | | Measured | Inferred |
| Rock Samples | | | | | | | |
| FB*-A | 0.223 | 11.3 | 33.0 | 16.12 | 0.065 | 2560 | 2860 |
| FB*-B | 0.168 | 18.8 | 30.0 | 14.65 | 0.105 | 1125 | 954 |
| FB*-C | 0.067 | 144.9 | 34.9 | 17.05 | 1.95 | 5.0 | 8.2 |
| Berea-A | 0.229 | 11.2 | 42.5 | 20.76 | 0.3 | 725 | 650 |
| Berea-B | 0.205 | 20.1 | 43.8 | 21.40 | 2.7 | 30 | 45.4 |
| White-stone | 0.260 | 15.9 | 13.0 | 6.35 | 8.8 | 3.678 | 4.711 |
| Lime-stone | 0.150 | 39.7 | 23.3 | 11.38 | 11.8 | 4.025 | 3.463 |
| Bandera | 0.219 | 16.9 | 31.7 | 15.48 | 60.5 | 3.59 | 1.734 |
| Glass Bead Samples | | | | | | | |
| SG-09 | 0.298 | 6.8 | 130.0 | 26.56 | 0.054 | 7407 | 7473 |
| C321-84 | 0.101 | 55.0 | 86.05 | 17.58 | 4.89 | 6.974 | 7.058 |

*FountainBleau

The inferred permeability is that as calculated by Eq. 8 using $K_1°$ and $K_2°$.
The measured permeability is that as measured directly by application of pressure $\Delta P_a$ and detecting the flow rate $\dot{Q}$ and applying Darcy's relation
$\dot{Q} = \upsilon A = \frac{k \Delta P}{\eta L} A$ where
A = cross sectional area of sample ; L = Length of sample $\eta$ = fluid viscosity; and k = sample permeability.

Figure 15:
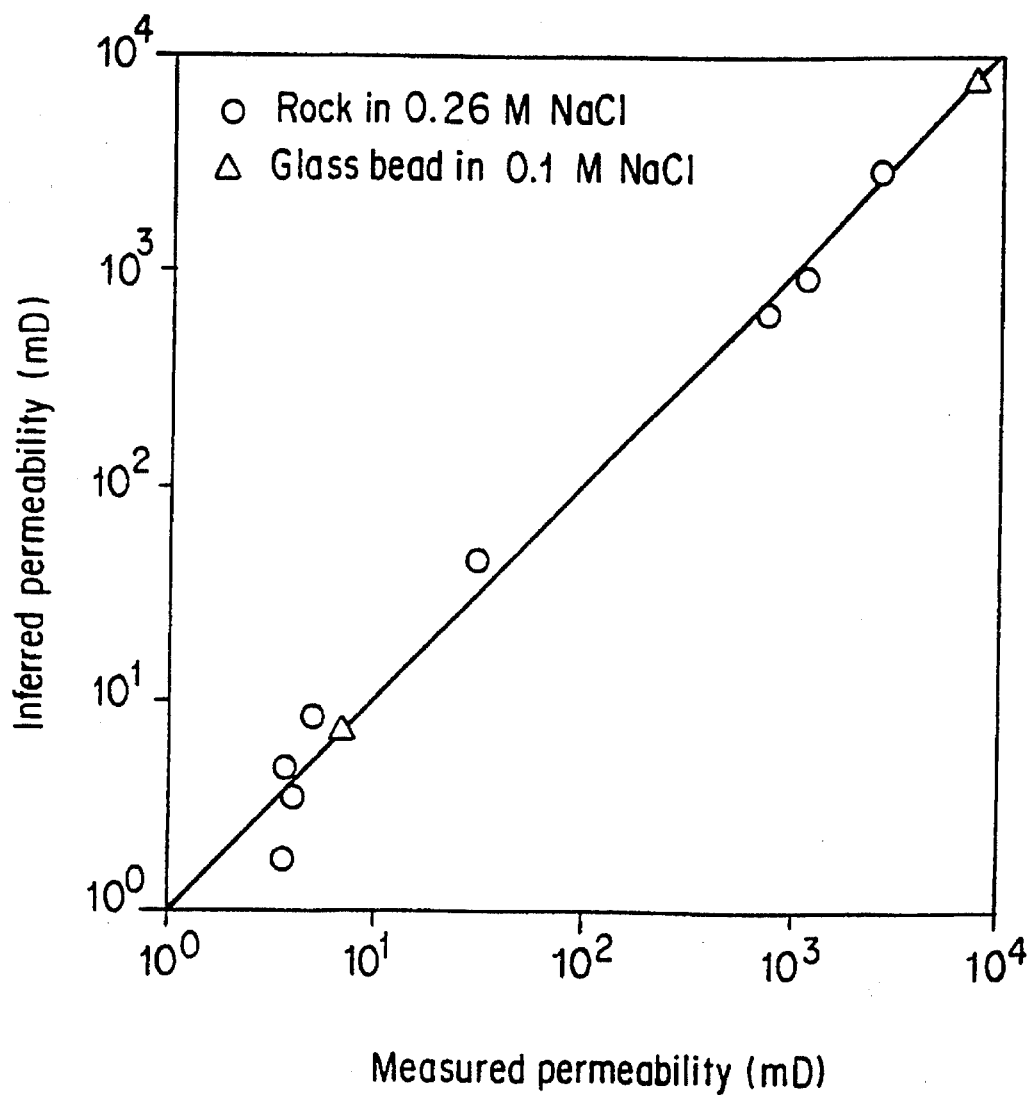
FIG. 15 shows permeability calculated from the low frequency streaming potential coefficient $K_1^o$, electro-osmosis coefficient $K_1^o$, and conductivity $\sigma_r^o$ according to this invention compared to direct permeability measurements.

Table 1 shows the wide range of formation permeabilities for which the a.c. process and apparatus of this invention is effective, particularly the lower permeabilities below about 10 milli-Darcies, which cannot be measured by the prior art d.c. processes or prior art a.c. processes where the application and detection electrodes are spaced, such as with one down the borehole and one on the surface. FIG. 15 is a plot of inferred permeability versus measured permeability.

While in the foregoing specification this invention has been described in relation to certain preferred embodiments thereof, and many details have been set forth for the purpose of illustration, it will be apparent to those skilled in the art that the invention is susceptible to additional embodiments and that certain of the details described herein can be varied considerably without departing from the basic principles of the invention.

I claim:

1. A process for measuring d.c. value of electro-osmosis coefficient $K_2°$ of porous media formations containing fluid comprising: applying a.c. current at any finite frequency to said porous media that also causes a corresponding a.c. voltage, measuring electro-osmosis in said porous media by measuring the relative amplitude A between the produced a.c. pressure and the applied a.c. voltage signals at said finite frequency using a differential pressure sensor and a pair of measurement electrodes near the application of said a.c. current, measuring the relative phase angle $\phi$ of said pressure and voltage signals by said pressure sensor and pair of measurement electrodes, and ascertaining said $K_2^o$ by the relation $K_2^o = A(1+\tan^2\phi)^{1/2}$.

2. A process according to claim 1 wherein said finite frequency has a range of values extending from about 0.01 to about 1000 Hz.

3. A process according to claim 1 wherein said measurement electrodes are in contact with the porous media formation through the fluid and spaced apart at a distance from the application point less than 1/10th of the wave length of the wave propagated by application of said a.c. voltage.

4. A process according to claim 1 wherein said measurement electrodes are spatially removed from formation fluid flow paths through said porous media.

5. A process for determining d.c. value of electro-osmosis coefficient $K_2^o$ of porous media formations containing fluid comprising: applying a plurality of sets of a.c. currents at different single angular frequencies $\omega$ to said porous media that also cause a corresponding plurality of sets of a.c. voltages, measuring the relative amplitude A between each set of produced a.c. pressure and applied a.c. voltage signals of each said different single angular frequency using a differential pressure sensor and a pair of measurement electrodes near the application of said a.c. current, and ascertaining said $K_2^o$ from a graph of emperical data by performing a least squares fit of data thus obtained for said relative amplitudes measured at the different single angular frequencies $\omega$ into the equation $A=K_2^o/(1+\omega^2\tau^2)^{1/2}$ using $\tau$ and $K_2^o$ as two independent fitting parameters, where $\tau$ is a characteristic relaxation time of the electro-osmosis signal.

6. A process according to claim 5 wherein said finite frequency has a range of values extending from about 0.01 to about 1000 Hz.

7. A process according to claim 5 wherein said measurement electrodes are in contact with the porous media formation through the fluid and spaced apart at a distance from the application point less than 1/10th of the wave length of the wave propagated by application of said a.c. voltage.

8. A process according to claim 5 wherein said measurement electrodes are spatially removed from formation fluid flow paths through said porous media.

9. A process for determining permeability k of porous media formations containing fluid comprising: applying a.c. current at a single angular frequency f to said porous media that also causes a corresponding a.c. voltage, measuring the relative phase angle $\phi$ of the produced a.c. pressure and the applied a.c. voltage signal at said single angular frequency using a differential pressure sensor and a pair of measurement electrodes near the application of said a.c. current, determining the relaxation frequency $f_0$ using $f_0 = f/\tan\phi$, and determining permeability k by the relation $k=Cf_0$ wherein C is a constant determined by making a measurement of $f_0$ using the same instrument on a given sample of porous media with known permeability k.

10. A process according to claim 9 wherein said finite frequency has a range of values extending from about 0.01 to about 1000 Hz.

11. A process according to claim 9 wherein said measurement electrodes are in contact with the porous media formation through the fluid and spaced apart at a distance from the application point less than 1/10th of the wave length of the wave propagated by application of said a.c. voltage.

12. A process according to claim 9 wherein said measurement electrodes are spatially removed from formation fluid flow paths through said porous media.

13. A process for determining permeability k of porous media containing fluid comprising: applying a plurality of sets of a.c. currents at different angular frequencies $\omega$ to said porous media that also cause a corresponding plurality of sets of a.c. voltages, measuring the relative amplitude A between each set of produced a.c. pressure and a.c. voltage signals at each said different single angular frequency using a differential pressure sensor and a pair of measurement electrodes near the application of said a.c. current, determining angular frequency $f_0$ by performing a least squares fit of the amplitude A from data thus obtained for said relative amplitudes measured at the different single angular frequencies $\omega$ according to the equation for $A=K_2^o/(1+\omega^2\tau^2)^{1/2}$ wherein $\tau=1/2\pi f_0$, and determining permeability k of empirical data on a graph by the relation $k=Cf_0$ wherein C is a constant determined by making a measurement of $f_0$ using the same instrument on a given sample of porous media with known permeability k.

14. A process according to claim 13 wherein said finite frequency has a range of values extending from about 0.01 to about 1000 Hz.

15. A process according to claim 13 wherein said measurement electrodes are in contact with the porous media formation through the fluid and spaced apart at a distance from the application point less than 1/10th of the wave length of the wave propagated by application of said a.c. voltage.

16. A process according to claim 13 wherein said measurement electrodes are spatially removed from formation fluid flow paths through said porous media.

17. A process for determination of the thickness of layered porous media formations containing fluid comprising: applying a plurality of sets of pressure oscillations at different frequencies to fluid in said porous media, measuring induced a.c. streaming potential voltage signal $V_s$ at each of said different frequencies of pressure oscillation using a pair of measurement electrodes near the application of said pressure, measuring differential fluid pressure $P_a$ in said porous media between said electrodes, determining $K_1$ by the relation $V_s/P_a$, determining characteristic frequency $f_s$ by a maximal change of $K_1$ with respect to frequency, determining the thickness of the layer adjacent said application of pressure oscillations by determining the penetration distance L by the relation $L^2 = D_{adjacent\ medium}/2\pi f_s$ wherein $D_{adjacent\ medium}$ is the pressure diffusion constant of the medium adjacent to the pressure source.

18. A process according to claim 17 wherein said finite frequency has a range of values extending from about 0.01 to about 1000 Hz.

19. A process according to claim 17 wherein said measurement electrodes are in contact with the porous media formation through the fluid and spaced apart at a distance from the application point less than 1/10th of the wave length of the wave propagated by application of said pressure oscillations.

20. A process according to claim 17 wherein said measurement electrodes are spatially removed from formation fluid flow paths through said porous media.

21. A process for determination of the thickness of mudcake lining a borehole comprising: applying a plurality of sets of pressure oscillations at different frequencies to fluid in said mudcake, measuring induced a.c. STP voltage signal $V_s$ at each of said different frequencies of pressure oscillation using a pair of measurement electrodes near the application of said pressure, measuring differential fluid pressure $P_a$ in said porous media between said electrodes, determining characteristic frequency $f_s$ at the change between these two values, determining $K_1$ by the relation $V_s/P_a$, determining the thickness of said mudcake adjacent said application of pressure oscillations by determining the penetration distance L by the relation $L^2 = D_{mudcake}/2\pi f_s$ wherein $D_{mudcake}$ is the pressure diffusion constant of the mudcake.

22. A process according to claim 21 wherein said finite frequency has a range of values extending from about 0.01 to about 1000 Hz.

23. A process according to claim 21 wherein said measurement electrodes are in contact with the porous media formation through the fluid and spaced apart at a distance from the application point less than 1/10th of the wave length of the wave propagated by application of said pressure oscillations.

24. A process according to claim 21 wherein said measurement electrodes are spatially removed from formation fluid flow paths through said porous media.

25. A process having reduced effect of mudcake lining on a borehole wall in measuring streaming potential coefficient $K_1$ of porous rock formations containing fluid comprising: applying pressure oscillations at a finite frequency to said fluid from chambers at opposite ends of a plurality of adjacent chambers, measuring induced a.c. voltage signal $V_s$ at said finite frequency using a pair of measurement electrodes in two adjacent interior chambers spaced from said chambers at opposite ends, measuring differential fluid pressure $P_a$ in said porous rock formation by differential pressure sensors in said two adjacent interior chambers, and ascertaining said $K_1$ by the relation $K_1 = V_s/P_a$ wherein $V_s$ is the measured a.c. streaming potential voltage signal and $P_a$ is the measured applied pressure differential.

26. A process according to claim 25 wherein said finite frequency has a range of values extending from about 0.01 to about 1000 Hz.

27. A process according to claim 25 wherein said measurement electrodes are in contact with the porous media formation through the fluid and spaced apart at a distance from the application point less than 1/10th of the wave length of the wave propagated by application of said pressure oscillations.

28. A process according to claim 25 wherein said measurement electrodes are spatially removed from formation fluid flow paths.

29. An apparatus for in-situ down the hole determination of permeability k of porous rock formation containing fluid providing reduced effect of mudcake lining a borehole wall comprising: chamber walls forming a plurality of four and greater adjacent chambers comprising a first end chamber, a second opposite end chamber, and at least two inner chambers between said first end and said second end chambers, each said chamber having an opening on one side adjacent said mudcake of said porous rock formation; sealing means around each said opening capable of forming a generally fluid-tight seal with a face of said mudcake of said porous rock formation thereby isolating each said fluid chamber from fluid communication with each other except through said mudcake and porous rock formation; means for applying pressure oscillations at a finite frequency through fluid in said first and second end chambers to fluid in said porous rock formation in a streaming potential mode of operation, the differential pressure between said end chambers being monotonic and the two pressure sources operated 180° out-of-phase; current electrode means in said first and second end chambers for applying a.c. current at a finite frequency between said end chambers through fluid in said porous rock formation in an electro-osmosis mode of operation that also causes a corresponding a.c. voltage; means for measuring induced streamed potential a.c. voltage with measurement voltage electrodes located in each of said end chambers and said inner chambers for sensing induced differential a.c. voltage signal between each pair of chambers at said finite frequency of said applied pressure oscillations in said streaming potential mode and capable of measuring electro-osmosis a.c. applied voltage signal in said electro-osmosis mode; and fluid pressure sensing means between each pair of said adjacent chambers for sensing and measuring differential fluid pressure between each said pair of chambers.

30. An apparatus according to claim 29 wherein said means for applying pressure oscillations comprises an electro-mechanical transducer capable of producing pressure oscillations at a frequency within the range of about 0.01 to about 1000 Hz and is powered by an oscillating voltage.

31. An apparatus according to claim 29 wherein said means for measuring induced streaming potential a.c. voltage comprises said measurement electrodes supplying differential voltage signals to a lock-in amplifier or digital frequency response analyzer capable of measurement of said voltage signals at said finite frequency to obtain phase and amplitude of said voltage signals to levels below 1 μV.

32. An apparatus according to claim 29 wherein said means for measurement of said differential fluid pressure comprises a piezoresistive or piezoelectric transducer.

33. An apparatus according to claim 29 wherein said measurement electrodes are in contact with the porous rock formation through the fluid and spaced apart at a distance of 1/10th of the wave length and less of the wave propagated by application of said pressure oscillations from their application points.

34. An apparatus according to claim 29 wherein said means for applying a.c. current comprises an oscillator supplying oscillating voltage with a corresponding oscillating current at a frequency within the range of about 0.01 to about 1000 Hz to a current electrode.

35. An apparatus according to claim 29 wherein said means for measuring induced electro-osmotic voltage comprises said measurement electrodes supplying differential voltage signals to a lock-in amplifier or digital frequency response analyzer capable of measurement of said voltage signals at said finite frequency to obtain phase and amplitude of said voltage signals to levels below 1 μV.

36. An apparatus according to claim 29 further comprising a.c. current supply and current electrode means for application of a.c. current to said rock formation in a rock conductivity mode of measurement and measurement means for phase and amplitude measurement of voltage and current in said conductivity mode of measurement.

37. An apparatus according to claim 36 further comprising switching means capable of switching 1) said voltage electrode to said measurement means for measuring induced streaming potential voltage a.c. signal at said finite frequency of said applied pressure oscillations in said streaming potential mode of measurement, and said fluid pressure means to said measurement means for measuring differential fluid pressure, 2) said voltage electrode to said measurement means for measuring induced electro-osmotic voltage a.c. signal at said finite frequency of said applied a.c. voltage signal in said electro-osmotic mode of measurement, and said fluid pressure means to said measurement means for measuring differential fluid pressure, and 3) said voltage electrode and a current electrode to said measurement means for measuring phase and amplitude of an a.c. signal in rock conductivity mode of measurement.

38. A process for determination of permeability k of porous media formation comprising:

measuring streaming potential coefficient $K_1$ of said porous media formation comprising, applying pressure oscillations at a finite frequency to fluid in said porous media formation that also causes a corresponding a.c. voltage, measuring streaming potential in said porous media formation by measurement of the induced a.c. voltage signal at said finite frequency using a pair of measurement electrodes near the application of said pressure, measuring differential fluid pressure in said porous media formation between said electrodes, and ascertaining said $K_1$ by the relation $K_1=V_s/P_a$ wherein $V_s$ is the measured streaming potential voltage and $P_a$ is the applied pressure difference;

measuring d.c. value of electro-osmosis coefficient $K_2^o$ of said porous media formation comprising, applying a.c. current at any finite frequency to said porous media formation, measuring electro-osmosis in said porous media formation by measuring the relative amplitude A between the produced a.c. pressure and the applied a.c. voltage signals at said finite frequency using a differential pressure sensor and a pair of measurement electrodes near the application of said a.c. current, measuring the relative phase angle $\phi$ of said pressure and voltage signals by said pressure sensor and pair of measurement electrodes and ascertaining said $K_2^o$ by the relation $K_2^o=A(1+\tan^2\phi)^{1/2}$;

ascertaining said porous media formation permeability k by the relation $k=\eta\sigma_r K_1/K_2^o$ wherein $\eta$ is viscosity of fluid in said porous media formation and $\sigma_r$ is conductivity of fluid saturated said porous media formation.

39. A process according to claim 38 wherein said finite frequency has a range of values extending from about 0.01 to about 1000 Hz.

40. A process according to claim 38 wherein said measurement electrodes are in contact with the porous media formation through the fluid and spaced apart at a distance from the application point less than 1/10th of the wave length of the wave propagated by application of said pressure oscillations.

41. A process according to claim 38 wherein said measurement electrodes are spatially removed from formation fluid flow paths through said porous media.

42. A process for determination of permeability k of porous media formation comprising:

measuring streaming potential coefficient $K_1$ of said porous media formation comprising, applying pressure oscillations at a finite frequency to fluid in said porous media formation, measuring streaming potential in said porous media formation by measurement of the induced a.c. voltage signal at said finite frequency using a pair of measurement electrodes near the application of said pressure, measuring differential fluid pressure in said porous media formation between said electrodes, and ascertaining said $K_1$ by the relation $K_1=V_s/P_a$ wherein $V_s$ is the measured streaming potential voltage and $P_a$ is the applied pressure difference;

determining d.c. value of electro-osmosis coefficient $K_2^o$ of said porous media formation containing fluid comprising, applying a plurality of sets of a.c. currents at different single angular frequencies $\omega$ to said porous media formation that also causes a corresponding plurality of sets of a.c. voltages, measuring the relative amplitude A between each set of produced a.c. pressure and applied a.c. voltage signals of each said different single angular frequency using a differential pressure sensor and a pair of measurement electrodes near the application of said a.c. current and ascertaining said $K_2^o$ from a graph of empirical data by performing a least squares fit of data thus obtained for said relative amplitudes measured at the different single angular frequencies into the equation $A=K_2^o/(1+\omega^2\tau^2)^{1/2}$ using $\tau$ and $K_2^o$ as two independent fitting parameters, where is a characteristic relaxation time of the electro-osmosis signal; ascertaining said porous media formation permeability k by the relation $k=\eta\sigma_r K_1/K_2^o$ wherein $\eta$ is viscosity of fluid in said porous media formation and $\sigma_r$ is conductivity of fluid saturated said porous media formation.

43. A process according to claim 42 wherein said finite frequency has a range of values extending from about 0.01 to about 1000 Hz.

44. A process according to claim 42 wherein said measurement electrodes are in contact with the porous media formation through the fluid and spaced apart at a distance from the application point less than 1/10th of the wave length of the wave propagated by application of said pressure oscillations.

45. A process according to claim 42 wherein said measurement electrodes are spatially removed from formation fluid flow paths through said porous media.

\* \* \* \* \*

UNITED STATES PATENT AND TRADEMARK OFFICE
CERTIFICATE OF CORRECTION

PATENT NO. : 5,503,001
DATED : April 02, 1996
INVENTOR(S) : Po-zen WONG

It is certified that error appears in the above-indentified patent and that said Letters Patent is hereby corrected as shown below:

At column 20, line 11, in Claim 29, please delete the word "streamed" and in its place insert --streaming--.

Signed and Sealed this

First Day of October, 1996

Attest:

BRUCE LEHMAN

*Attesting Officer*     *Commissioner of Patents and Trademarks*